United States Patent [19]

Williams et al.

[11] Patent Number: 5,527,819
[45] Date of Patent: Jun. 18, 1996

[54] INHIBITORS OF HIV REVERSE TRANSCRIPTASE

[75] Inventors: Theresa M. Williams, Harleysville; Terrence M. Ciccarone, East Greenville; Walfred S. Saari, Lansdale; John S. Wai, Harleysville, all of Pa.; William J. Greenlee, Teaneck, N.J.; Suresh K. Balani, Hatfield, Pa.; Mark E. Goldman, San Diego, Calif.; Anthony D. Theoharides, deceased, late of Lansdale, Pa., by Sharon A. Theoharides, executrix; Jacob M. Hoffman, Jr., Landsale, Pa.; William C. Lumma, Jr., Pennsburg, Pa.; Joel R. Huff, Gwynedd Valley, Pa.; Clarence S. Rooney, Worcester, Pa.; Philip E. Sanderson, Philadelphia, Pa.

[73] Assignee: Merck & Co., Inc., Rahway, N.J.

[21] Appl. No.: 488,957

[22] Filed: Jun. 7, 1995

Related U.S. Application Data

[63] Continuation of Ser. No. 274,101, Jul. 11, 1994, abandoned, which is a continuation of Ser. No. 21,925, Feb. 24, 1993, abandoned, which is a continuation-in-part of Ser. No. 866,765, Apr. 9, 1992, abandoned, which is a continuation-in-part of Ser. No. 832,260, Feb. 7, 1992, abandoned, which is a continuation-in-part of Ser. No. 756,013, Sep. 6, 1991, abandoned.

[51] Int. Cl.$^6$ .................. C07D 209/30; A61K 31/40
[52] U.S. Cl. .................................. 514/419; 548/492
[58] Field of Search .................... 548/492; 514/419

[56] References Cited

U.S. PATENT DOCUMENTS

| | | | |
|---|---|---|---|
| 4,255,442 | 3/1981 | Steinman et al. | 424/274 |
| 4,873,259 | 10/1989 | Summers, Jr. et al. | 514/443 |
| 5,124,327 | 6/1992 | Greenlee et al. | 514/235.2 |

FOREIGN PATENT DOCUMENTS

| | | | |
|---|---|---|---|
| 0000972 | 3/1979 | European Pat. Off. | 548/484 |
| 0275667 | 7/1988 | European Pat. Off. | 548/484 |
| 1935671 | 3/1970 | Germany | 548/484 |
| WO88/08424 | 11/1988 | WIPO | 546/132 |
| WO91/05761 | 5/1991 | WIPO | 548/484 |
| WO91/09849 | 7/1991 | WIPO | 548/484 |
| WO92/13863 | 8/1992 | WIPO | 548/484 |

OTHER PUBLICATIONS

Savena, et al., J. Medicinal Chemistry, vol. 12, pp. 1120–1122 (1969).
Uhlendorf, et al., Chemical Abstracts, vol. 110, No. 25, Abstract No. 231432y (1989).
Chemical Abstracts, CA 117(21):212489a, 1992.
Inaba et al., Chem. Pharm. Bull., 24, 1076–1082 (1976).
Atkinson et al., Synthesis, 480–481 (Jun. 1988).
Nagarathnam et al., Synthesis, No. 11, 926–927 (Nov. 1982).
Mohan et al., Synthesis, No. 2, 188–190 (Feb. 1985).
Vedachalam, M., Tet. Letters, 24, 3531–3532 (1983).
Nagarathnam et al., Synthesis, No. 2, pp. 156–157 (Feb. 1983).
Selvakumaren et al., India J. of Chem., 24B, 692 (1985).
Ratner et al., Nature, 313, 277 (1985).
Toh et al., EMBO J., 4, 1267 (1985).
Power et al., Science, 231, 1567 (1986).
Pearl et al., Nature, 329 351 (1987).
Shvedov, V. I., et al., Chemical Abstracts, vol. 72, pp. 313–314, AB#12471D, (1970).
Dave, V., Chemical Abstracts, vol. 85, p. 374, AB#32754V, (1976).
Tomita, K., et al., Chemical Abstracts, vol. 87, p. 705, AB#135057R, (1977).
Banerji, A. et al., Chemical Abstracts, vol. 90, p. 575, AB#6272V, (1979).
Gairns, R. S., et al., Chemical Abstracts, vol. 106, p. 616, AB#49926C, (1987).
Atkinson, J. G., et al., Chemical Abstracts, vol. 109, p. 710, AB#149279Z, (1988).
Wojciechowski, K. et al., Chemical Abstracts, vol. 106, p. 618, AB#119608B, (1987).
Lewis, M. G. et al., Chemical Abstracts, vol. 104, p. 26, AB#61594J, (1986).
D. L. Romero, et al., Proc. Natl. Acad. Sci. USA, vol. 88, pp. 8806–8810, (Oct. 1991).
Houlihan et al, Indole (Part III), pp. 306, 309, 310, 314, 315, 461, 462, 476, 477 (1979).

*Primary Examiner*—C. Warren Ivy
*Assistant Examiner*—Zinna N. Davis
*Attorney, Agent, or Firm*—Carol S. Quagliato; Roy D. Meredith; Charles M. Caruso

[57] ABSTRACT

Novel indole compounds inhibit HIV reverse transcriptase, and are useful in the prevention or treatment of infection by HIV and the treatment of AIDS, either as compounds, pharmaceutically acceptable salts, pharmaceutical composition ingredients, whether or not in combination with other antivirals, anti-infectives, immunomodulators, antibiotics or vaccines. Methods of treating AIDS and methods of preventing or treating infection by HIV are also described.

9 Claims, No Drawings

INHIBITORS OF HIV REVERSE TRANSCRIPTASE

This is a continuation of application Ser. No. 08/274,101 filed on Jul. 11, 1994, now abandoned, which is a continuation of application Ser. No. 08/021,925 filed on Feb. 24, 1993, now abandoned, which is a continuation-in-part of co-pending application U.S. Ser. No. 07/866,765 filed Apr. 9, 1992 now abandoned, which itself is a continuation-in-part of application U.S. Ser. No. 07/832,260 filed Feb. 7, 1992 and now abandoned, which itself was a continuation-in-part of application U.S. Ser. No. 07/756,013, filed Sep. 6, 1991, now abandoned.

The present invention is concerned with compounds which inhibit the reverse transcriptase encoded by human immunodeficiency virus (HIV) or pharmaceutically acceptable salts thereof and are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS and vital infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a vitally encoded reverse transcriptase to generate DNA copies of HIV sequences, a required step in vital replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Rather, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compounds of this invention are inhibitors of HIV reverse transcriptase. Furthermore, the compounds of the present invention do not require bioactivation to be effective.

BRIEF DESCRIPTION OF THE INVENTION

Novel compounds of formula A:

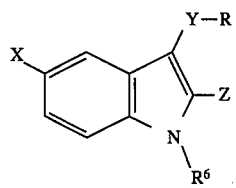

as herein defined, are disclosed. These compounds are useful in the inhibition of HIV reverse transcriptase, the prevention of infection by HIV, the treatment of infection by HIV and in the treatment of AIDS and/or ARC, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with the compounds of formula A described below, combinations thereof, or pharmaceutically acceptable salts or esters thereof, in the inhibition of HIV reverse transcriptase, the prevention or treatment of infection by HIV and in the treatment of the resulting acquired immune deficiency syndrome (AIDS). The compounds of this invention include those with structural formula A:

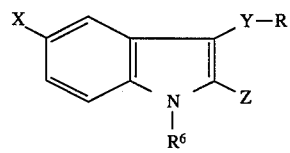

wherein

X is —H, —Cl, —F, —Br, —NO$_2$, —CN, —OR$^2$, —NR$^2$R$^2$, —NHSO$_2$—C$_{1-3}$alkyl, or —NHCO—C$_{1-3}$alkyl;

Y is —S(O)$_n$— or —O—, wherein n is zero, 1 or 2;

R is
1) —C$_{1-5}$alkyl, unsubstituted or substituted with one or more of:
   a) —C$_{1-5}$alkyl,
   b) —C$_{1-5}$alkoxy,
   c) —OH, or
   d) aryl, unsubstituted or substituted with one or more of:
      i) —C$_{1-5}$alkyl,
      ii) —C$_{1-5}$alkoxy,
      iii) —OH,
      iv) halogen, or
      v) —NR$^2$R$^2$,
2) aryl, unsubstituted or substituted with one or more of:
   a) —C$_{1-5}$alkyl, unsubstituted or substituted with one or more of:
      i) —OH or
      ii) —C$_{1-5}$alkoxy,
   b) —C$_{1-5}$alkoxy,
   c) —OH,
   d) halogen, or
   e) —NR$^2$R$^2$,
3) heterocycle, unsubstituted or substituted with one or more of:
   a) —C$_{1-5}$alkyl, unsubstituted or substituted with one or more of:
      i) —OH or
      ii) —C$_{1-5}$alkoxy,
   b) —C$_{1-5}$alkoxy,
   c) —OH,
   d) halogen, or
   e) —NR$^2$R$^2$, or
4) —NR$^2$R$^3$, provided that Y is —S(O)$_n$—;

Z is

1)

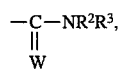

wherein W is O, S, —N—CN, or —N—OR$^2$,
2) —COR$^{1a}$,
3) —COOR$^{1b}$,
4) —CR$^2$R$^2$—S(O)$_n$—R$^{1a}$,
wherein n is defined above,
5) —CR$^2$R$^2$NHR$^4$,
6) —CR$^2$R$^2$—CO—R$^5$,
7) —C$_{1-3}$alkyl substituted with one or more of:
  a) aryl, unsubstituted or substituted with one or more of:
    i) —C$_{1-5}$alkyl,
    ii) —C$_{1-5}$alkoxy,
    iii) —OH,
    iv) halogen, or
    v) —NR$^2$R$^2$, or
  b) heterocycle, unsubstituted or substituted with one or more of:
    i) —C$_{1-5}$alkyl,
    ii) —C$_{1-5}$alkoxy,
    iii) —OH,
    iv) halogen, or
    v) —NR$^2$R$^2$, or
8) —CN;
R$^1$ is
1) hydrogen,
2) —C$_{1-5}$alkyl, unsubstituted or substituted with one or more of:
  a) —C$_{1-5}$alkyl,
  b) —C$_{1-5}$alkoxy,
  c) —OH,
  d) aryl unsubstituted or substituted with one or more of:
    i) —C$_{1-5}$alkyl,
    ii) —C$_{1-5}$alkoxy,
    iii) —OH
    iv) halogen, or
    v) —NR$^2$R$^2$, or
  e) heterocycle, unsubstituted or substituted with one or more of:
    i) —C$_{1-5}$alkyl,
    ii) —C$_{1-5}$alkoxy,
    iii) —OH,
    iv) halogen, or
    v) —NR$^2$R$^2$, or
3) aryl, unsubstituted or substituted with one or more of:
  a) —C$_{1-5}$alkyl, unsubstituted or substituted with one or more of:
    i) —OH or
    ii) —C$_{1-5}$alkoxy,
  b) —C$_{1-5}$alkoxy,
  c) —OH,
  d) halogen,
  e) —CN,
  f) —NO$_2$, or
  g) —NR$^2$R$^2$; or
4) heterocycle, unsubstituted or substituted with one or more of:
  a) —C$_{1-5}$alkyl, unsubstituted or substituted with one or more of:
    i) —OH or
    ii) —C$_{1-5}$alkoxy,
  b) —C$_{1-5}$alkoxy,
  c) —OH,
  d) halogen, or
  g) —NR$^2$R$^2$;
R$^{1a}$ is
1) —C$_{1-5}$alkyl, unsubstituted or substituted with one or more of:
  a) —C$_{1-5}$alkyl,
  b) —C$_{1-5}$alkoxy,
  c) —OH,
  d) aryl, unsubstituted or substituted with one or more of:
    i) —C$_{1-5}$alkyl,
    ii) —C$_{1-5}$alkoxy,
    iii) —OH,
    iv) halogen, or
    v) —NR$^2$R$^2$, or
  e) heterocycle, unsubstituted or substituted with one or more of:
    i) —C$_{1-5}$alkyl,
    ii) —C$_{1-5}$alkoxy,
    iii) —OH,
    iv) halogen, or
    v) —NR$^2$R$^2$, or
2) aryl, unsubstituted or substituted with one or more of:
  a) —C$_{1-5}$alkyl, unsubstituted or substituted with one or more of:
    i) —OH or
    ii) —C$_{1-5}$alkoxy,
  b) —C$_{1-5}$alkoxy,
  c) —OH,
  d) halogen,
  e) —CN,
  f) —NO$_2$, or
  g) —NR$^2$R$^2$;
3) heterocycle, unsubstituted or substituted with one or more of:
  a) —C$_{1-5}$alkyl, unsubstituted or substituted with one or more of:
    i) —OH or
    ii) —C$_{1-5}$alkoxy,
  b) —C$_{1-5}$alkoxy, or
  c) —OH,
  d) halogen, or
  e) —NR$^2$R$^2$, or
4) C$_{3-6}$cycloalkyl;
R$^{1b}$ is
1) —C$_{1-5}$alkyl substituted with one or more of:
  a) —C$_{1-5}$alkoxy,
  b) —OH,
  c) aryl, unsubstituted or substituted with one or more of:
    i) —C$_{1-5}$alkyl,
    ii) —C$_{1-5}$alkoxy,
    iii) —OH,
    iv) halogen, or
    v) —NR$^2$R$^2$, or
  d) heterocycle, unsubstituted or substituted with one or more of:
    i) —C$_{1-5}$alkyl,
    ii) —C$_{1-5}$alkoxy,
    iii) —OH,
    iv) halogen, or
    v) —NR$^2$R$^2$,
2) aryl, unsubstituted or substituted with one or more of:
  a) —C$_{1-5}$alkyl, unsubstituted or substituted with one or more of:

i) —OH or
ii) —C$_{1-5}$alkoxy,
b) —C$_{1-5}$alkoxy,
c) —OH,
d) halogen,
e) —CN,
f) —NO$_2$, or
g) —NR$^2$R$^2$; or
3) heterocycle, unsubstituted or substituted with one or more of:
a) —C$_{1-5}$alkyl, unsubstituted or substituted with one or more of:
i) —OH or
ii) —C$_{1-5}$alkoxy,
b) —C$_{1-5}$alkoxy,
c) —OH,
d) halogen, or
e) —NR$^2$R$^2$;

R$^2$ is hydrogen or C$_{1-3}$alkyl;
R$^3$ is
1) —C$_{1-5}$alkyl, unsubstituted or substituted with one or more of:
a) —C$_{1-5}$alkyl,
b) —C$_{1-5}$alkoxy, unsubstituted or substituted with —OH,
c) —OH,
d) —OC(O)R$^7$,
e) —COOR$^2$
f) aryl, unsubstituted or substituted with one or more of:
i) —C$_{1-5}$alkyl, unsubstituted or substituted with one or more of —OH,
ii) —C$_{1-5}$alkoxy,
iii) —OH,
iv) halogen,
v) —NO$_2$,
vi) —NR$^2$R$^2$,
vii) —NHCO—C$_{1-3}$alkyl, or
viii) —NHSO$_2$—C$_{1-3}$alkyl,
g) heterocycle, unsubstituted or substituted with one or more of:
i) —C$_{1-5}$alkyl,
ii) —C$_{1-5}$alkoxy,
iii) —OH,
iv) C$_{1-3}$alkyl—NR$^2$R$^2$,
v) halogen,
vi) oxo,
vii) —NO$_2$,
viii) —NR$^2$R$^2$,
ix) —NHCO—C$_{1-3}$alkyl, or
x) —NHSO$_2$—C$_{1-3}$alkyl,
h) —NR$^2$R$^2$,
i) —C$_{3-6}$cycloalkyl,
2) aryl, unsubstituted or substituted with one or more of:
a) —C$_{1-5}$alkyl,
b) —C$_{1-5}$alkoxy,
c) —OH,
d) halogen, or
e) —NR$^2$R$^2$,
3) heterocycle, unsubstituted or substituted with one or more of:
i) —C$_{1-5}$alkyl,
ii) —C$_{1-5}$alkoxy,
iii) —OH,
iv) halogen, or
v) —NR$^2$R$^2$, 4) —C$_{1-5}$alkoxy,
5) —OH,
6) —C$_{3-6}$cycloalkyl, or
7) hydrogen;
R$^4$ is
1) R$^1$ or
2) —COR$^1$;
R$^5$ is
1) R$^1$,
2) —C$_{1-5}$alkoxy,
3) —NHR$^1$, or
4) heterocycle, unsubstituted or substituted with one or more of:
i) —C$_{1-5}$alkyl,
ii) —C$_{1-5}$alkoxy,
iii) —OH,
iv) halogen, or
v) —NR$^2$R$^2$;
R$^6$ is
1) hydrogen,
2) —COR$^1$,
3) —CONHR$^1$;
R$^7$ is
1) aryl, unsubstituted or substituted with one or more of —Cl, —Br, —OH, —OCH$_3$, or —CN, or
2) —C$_{1-5}$alkyl, unsubstituted or substituted with one or more of —OH or —NR$^2$R$^2$; and with the proviso that when X is —H, Y is —S, R is unsubstituted phenyl and R$^6$ is —H,
Z is not —CH$_2$—SO—Ph, —COH,

or a pharmaceutically acceptable salt or ester thereof.

One embodiment of this invention encompasses compounds of Formula A further limited to:
X is —H, —Cl or —F;
Y is —S(O)$_n$;
R is —Ph, —tolyl, 3-Cl-phenyl, 2-pyridyl or 2-thiazolyl;
R$^6$ is —H; and
Z is

—COOR$^{1b}$, —COR$^{1a}$, —CR$^2$R$^2$—S(O)$_n$—R$^{1a}$ or —C$_{1-3}$alkyl substituted with heterocycle.

One class of compounds within the first embodiment is further limited to compounds wherein
X is —H or —Cl;
Y is —S(O)$_n$—;
R is —Ph, —tolyl, 3-Cl-phenyl or 2-thiazolyl;
R$^6$ is —H; and
Z is
1)

$$-\underset{\underset{W}{\|}}{C}-NR^2R^3,$$

wherein R$^2$ is —H and W is —O, —S or —NCN, or

2) —CR²R²—SO—aryl, wherein the aryl group is unsubstituted or substituted with one or more of —C₁₋₅alkyl.

A sub-class of compounds within this class is further limited to compounds wherein
X is —Cl;
Y is —S(O)ₙ—;
n is 1 or 2;
R is —Ph, 3-Cl-phenyl or 2-thiazolyl;
R⁶ is —H;
Z is

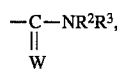

wherein R² is —H, and W is —O, —S or —NCN; and R³ is
1) —C₁₋₅alkyl, unsubstituted or substituted with one or more of
   a) —C₁₋₅alkoxy, unsubstituted or substituted with —OH,
   b) —OH,
   c) —OC(O)R⁷,
   d) aryl, unsubstituted or substituted with one or more of:
      i) —C₁₋₅alkyl, unsubstituted or substituted with one more of —OH,
      ii) —C₁₋₅alkoxy,
      iii) —OH,
      iv) halogen, or
      v) —NR²R²,
   e) heterocycle, unsubstituted or substituted with one or more of:
      i) —C₁₋₅alkyl,
      ii) —C₁₋₅alkoxy,
      iii) —OH,
      iv) halogen, or
      v) —NR²R², or
   f) C₃₋₆cycloalkyl,
2) heterocycle, unsubstituted or substituted with one or more of:
   i) —C₁₋₅alkyl,
   ii) —C₁₋₅alkoxy,
   iii) —OH,
   iv) halogen, or
   v) —NR²R²,
3) hydrogen, or
4) C₃₋₆ cycloalkyl.

A second embodiment of this invention encompasses compounds of formula A wherein X is selected from the group consisting of:
1) —NR²R²,
2) —NHSO—C₁₋₃alkyl, and
3) —NHCO—C₁₋₃alkyl.

A third embodiment of this invention encompasses compounds of formula A wherein Z is

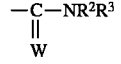

and R³ is selected from the group consisting of:
1) C₁₋₃alkyl substituted with phenyl wherein phenyl is substituted with one or more of:
   a) —NO₂,
   b) —NR²R²,
   c) —NHCO—C₁₋₃alkyl or
   d) —NHSO—C₁₋₃alkyl, and
2) C₁₋₃alkyl substituted with heterocycle, wherein heterocycle is substituted with one or more of:
   a) halogen,
   b) oxo,
   c) —NO₂,
   d) —NR²R²,
   e) —NHCO—C₁₋₃alkyl, or
   f) —NHSO₂—C₁₋₃alkyl.

A fourth embodiment of this invention encompasses compounds of formula A wherein Y is —S(O)ₙ— and R is —NR²R³.

The most preferred compounds of this invention are compounds 1 through 39, shown below.

Compound 1:

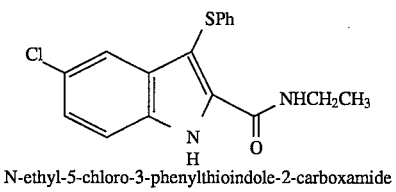

N-ethyl-5-chloro-3-phenylthioindole-2-carboxamide

Compound 2:

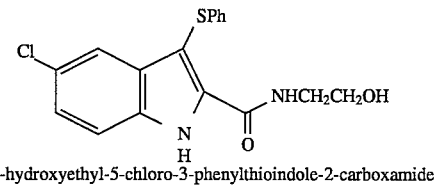

N-2-hydroxyethyl-5-chloro-3-phenylthioindole-2-carboxamide

Compound 3:

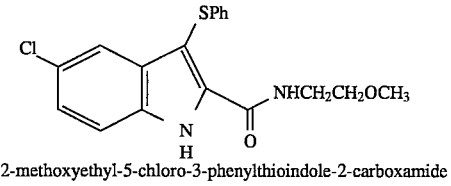

N-2-methoxyethyl-5-chloro-3-phenylthioindole-2-carboxamide

Compound 4:

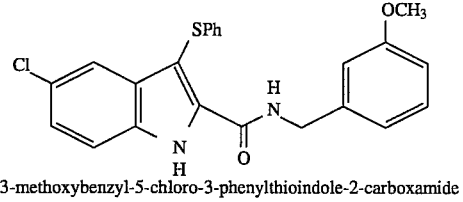

N-3-methoxybenzyl-5-chloro-3-phenylthioindole-2-carboxamide

Compound 5:

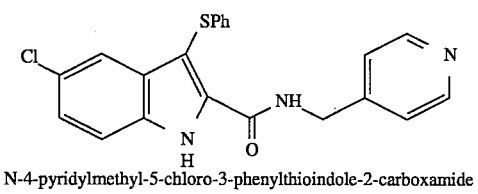

N-4-pyridylmethyl-5-chloro-3-phenylthioindole-2-carboxamide

Compound 6:

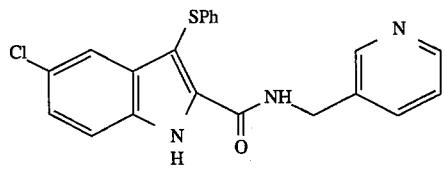

N-3-pyridylmethyl-5-chloro-3-phenylthioindole-2-carboxamide

Compound 7:

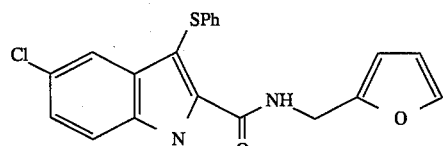

N-2-furanylmethyl-5-chloro-3-phenylthioindole-2-carboxamide

Compound 8:

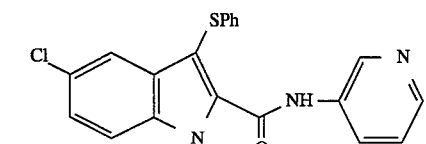

N-3-pyridyl-5-chloro-3-phenylthioindole-2-carboxamide

Compound 9:

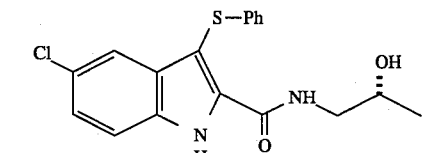

N-[1-(2(R)-hydroxypropyl)]-5-chloro-3-phenylthioindole-2-carboxamide

Compound 10:

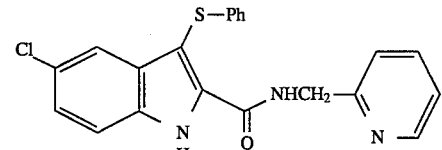

N-(2-pyridyl)methyl-5-chloro-3-phenylthioindole-2-carboxamide

Compound 11:

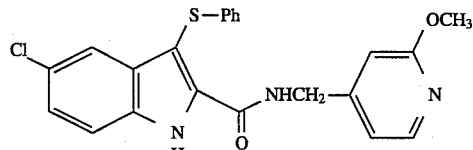

N-(3-methoxy-4-pyridyl)methyl-5-chloro-3-phenylthioindole-2-carboxamide

Compound 12:

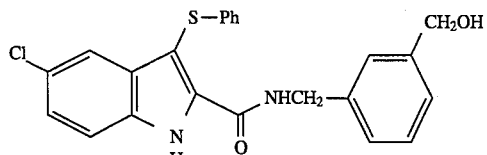

N-(3-hydroxymethyl)benzyl-5-chloro-3-phenyl-thioindole-2-carboxamide

Compound 13:

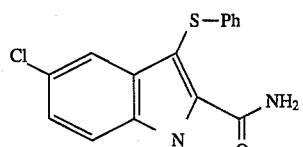

5-chloro-3-phenylthioindole-2-carboxamide

Compound 14:

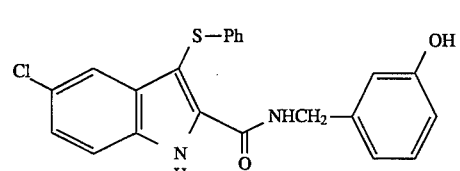

N-(3-hydroxybenzyl)-5-chloro-3-phenylthioindole-2-carboxamide

Compound 15:

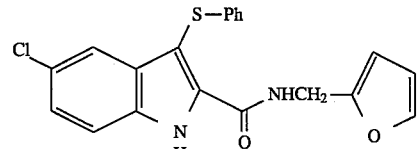

N-2-furanylmethyl-5-chloro-3-phenylthioindole-2-thiocarboxamide

Compound 16:

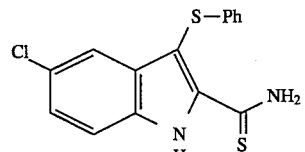

5-chloro-3-phenylthioindole-2-thiocarboxamide

Compound 17:

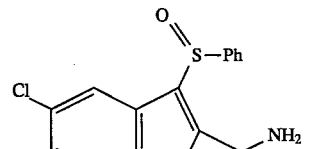

5-chloro-3-phenylsulfinylindole-2-carboxamide

Compound 18:

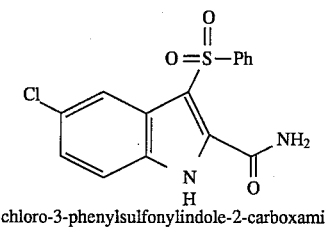

5-chloro-3-phenylsulfonylindole-2-carboxamide.

Compound 19:

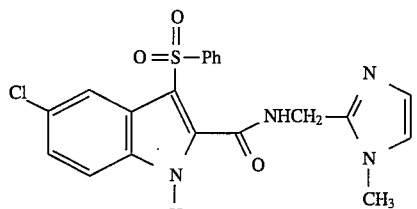

N-[(1-methylimidazol-2-yl)methyl]-3-phenylsulfonyl-5-chloroindole-2-carboxamide

Compound 20:

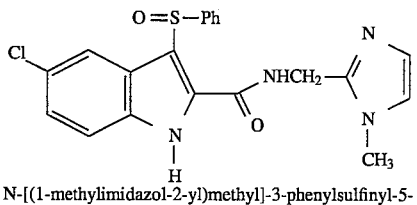

N-[(1-methylimidazol-2-yl)methyl]-3-phenylsulfinyl-5-chloroindole-2-carboxamide

Compound 21:

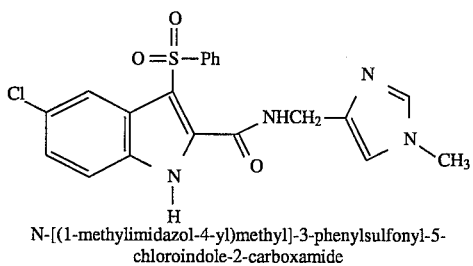

N-[(1-methylimidazol-4-yl)methyl]-3-phenylsulfonyl-5-chloroindole-2-carboxamide

Compound 22:

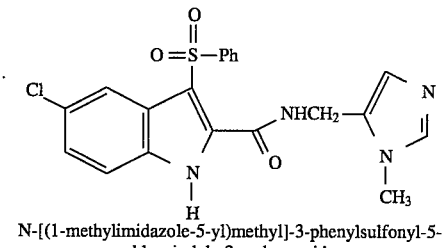

N-[(1-methylimidazole-5-yl)methyl]-3-phenylsulfonyl-5-chloroindole-2-carboxamide Compound 23:

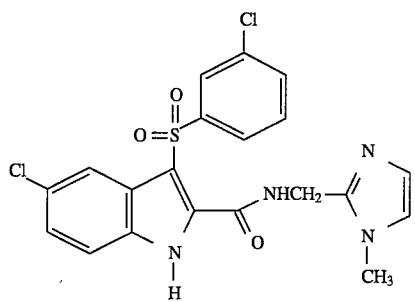

N-[(1-methylimidazol-2-yl)methyl]-3-(3-chlorophenyl-sulfony)-5-chloroindole-2-carboxamide Compound 24:

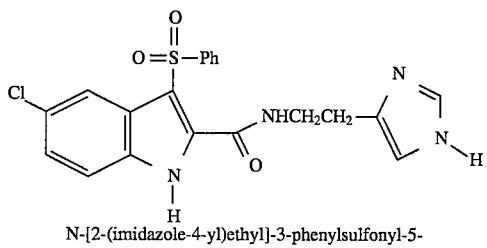

N-[2-(imidazole-4-yl)ethyl]-3-phenylsulfonyl-5-chloroindole-2-carboxamide

Compound 25:

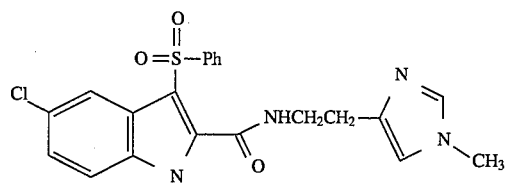

N-[2-(1-methylimidazole-4-yl)ethyl]-3-phenylsulfonyl-5-chloroindole-2-carboxamide Compound 26:

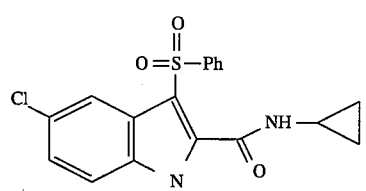

N-cyclopropyl-5-chloro-3-phenylsulfonylindole-2-carboxamide

Compound 27:

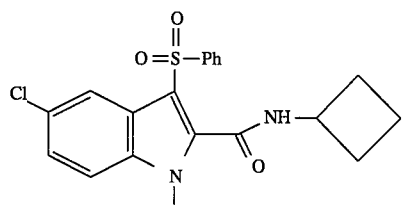

N-cyclobutyl-5-chloro-3-phenylsulfonylindole-2-carboxamide

Compound 28:

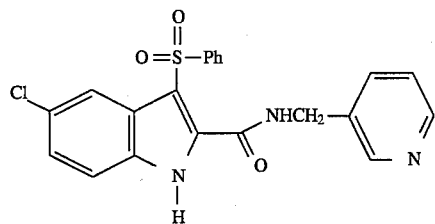

N-(3-pyridylmethyl)-3-phenylsulfonyl-5-chloroindole-2-carboxamide

Compound 29:

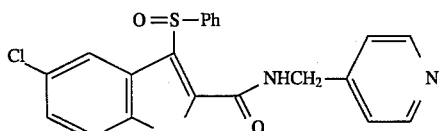

N-(4-pyridylmethyl)-5-chloro-3-phenylsulfinylindole-2-carboxamide

Compound 30:

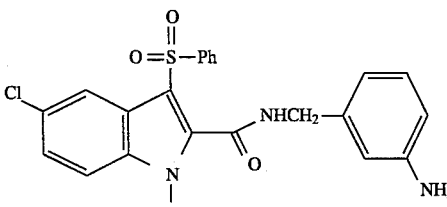

N-(3-aminobenzyl)-3-phenylsulfonyl-5-chloroindole-2-carboxamide

Compound 31:

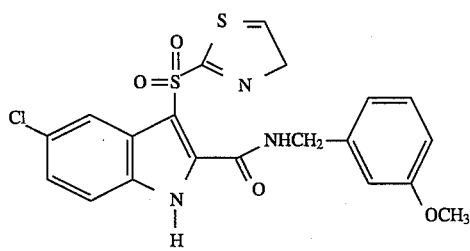

N-(3-methoxybenzyl)-5-chloro-3-(2-thiazolyl)sulfonyl-indole-2-carboxamide

Compound 32:

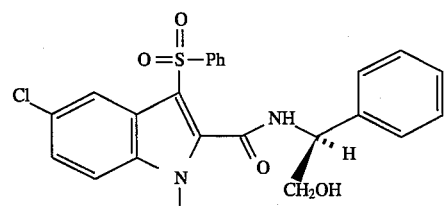

N-[(S)-1-phenyl-2-hydoxyethyl]-5-chloro-3-phenyl-sulfonylindole-2-carboxamide

Compound 33:

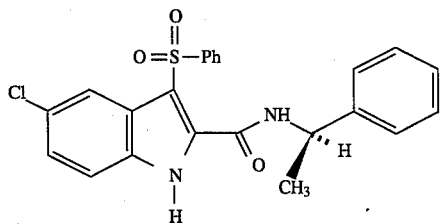

N-[(R)-1-phenylethyl]-5-chloro-3-phenylsulfonylindole-2-carboxamide

Compound 34:

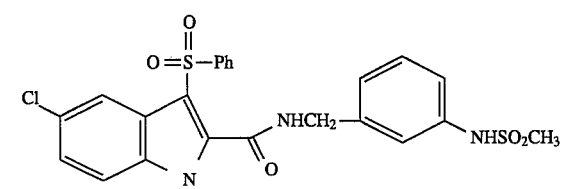

N-(3-methylsulfonylaminobenzyl)-3-phenylsulfonyl-5-chloroindole-2-carboxamide

Compound 35:

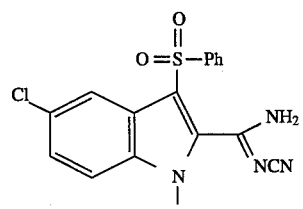

N-cyano-5-chloro-3-phenylsulfonylindole-2-carboximid-amide

Compound 36:

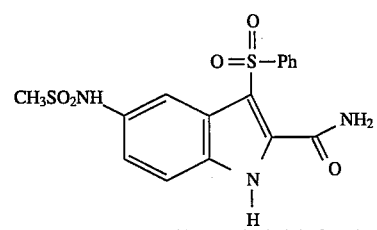

3-phenylsulfonyl-5-methylsulfonylaminoindole-2-carboxamide

Compound 37:

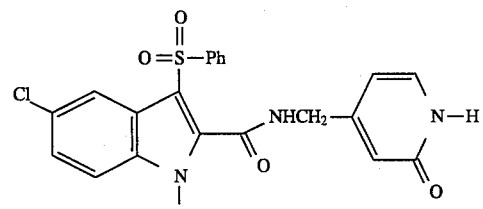

4-[(5-chloro-3-phenylsulfonylindole-2-carboxamido)-methyl]pyridin-2(1H)-one

Compound 38:

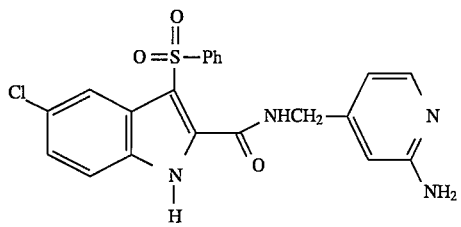

N-(2-amino-4-pyridylmethyl)-5-chloro-3-phenylsulfonyl-indole-2-carboxamide, and

Compound 39:

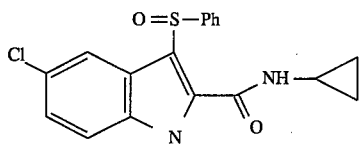

N-cyclopropyl-5-chloro-3-phenylsulfinylindole-2-carboxamide.

The compounds of the present invention may have asymmetric centers and occur as racemates, racemic mixtures, individual diastereomers, or enantiomers, with all isomeric forms being included in the present invention.

When any variable (e.g., aryl, heterocycle, $R^1$, $R^2$, $R^3$, etc.) occurs more than one time in any constituent or in formula A of this invention, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein, means fluoro, chloro, bromo and iodo.

As used herein, with exceptions as noted, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, biphenyl.

The term heterocycle or heterocyclic, as used herein except where noted, represents a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, benzofuranyl, tetrahydropyranyl, thienyl, benzothienyl, thiamorpholinyl, thiamorpholinyl sulfoxide, thiamorpholinyl sulfone, and oxadiazolyl.

Further abbreviations that may appear in this application are as follows:

| | |
|---|---|
| Me | methyl |
| Et | ethyl |
| Ph | phenyl |
| BuLi | butyllithium |
| n-Bu$_3$P | tri-n-butyl phosphine |
| LAH | lithium aluminum hydride |
| DMF | dimethylformamide |
| THF | tetrahydrofuran |
| Et$_3$N | tri-ethylamine |
| MMPP | monoperoxyphthalic acid, magnesium salt |
| BOP-reagent | benzotriazol-1-yloxytris-(dimethylamino)phosphonium hexafluorophosphate |
| mp or m.p. | melting point |

The pharmaceutically-acceptable salts of the novel compounds of this invention that are capable of salt formation (in the form of water- or oil-soluble or dispersible products) include the conventional non-toxic salts or the quaternary ammonium salts of these compounds, which are formed, e.g., from inorganic or organic acids or bases. Examples of such acid addition salts include acetate, adipate, alginate, aspartate, benzoate, benzenesulfonate, bissulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, pictate, pivalate, propionate, succinate, tartrate, thiocyanate, tosylate, and undecanoate. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Esters are also encompassed by the present invention, and include those which would readily occur to the skilled artisan, for example, $C_{1-4}$ alkyl esters.

Schemes I–VIII for preparing the novel compounds of this invention are presented below. Tables I–VII which follow the schemes illustrate the compounds that can be synthesized by Schemes I–VIII, but Schemes I–VIII are not limited by the compounds in the tables nor by any particular substituents employed in the schemes for illustrative purposes. The examples specifically illustrate the application of the following schemes to specific compounds.

Scheme I, below, is a general route for synthesizing, e.g., the compounds shown in Table I, infra. The substituent groups (e.g., X, R, $R^1$, etc.) employed in Scheme I correspond to the substituent groups as defined in Table I, but Scheme I is not limited by the defined substituents or compounds of Table I.

SCHEME I

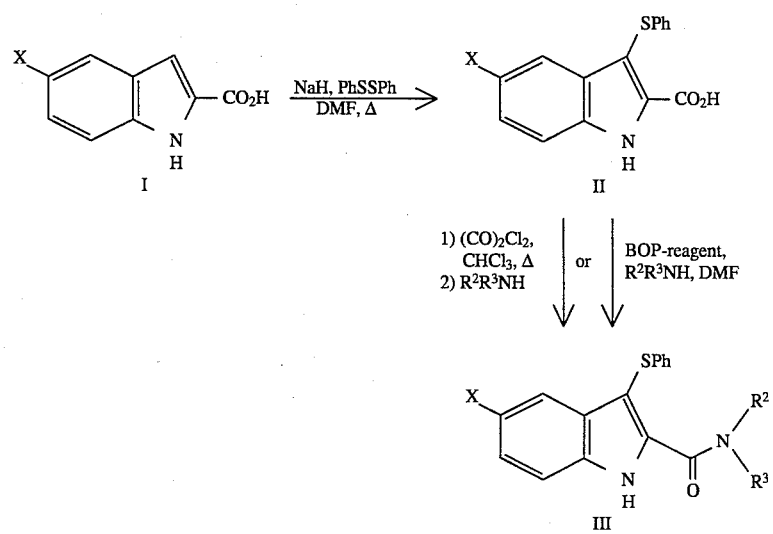

As shown in Scheme I, commercially available indole-2-carboxylic acid (or 5-chloro, 5-fluoro or 5-methoxyindole-2-carboxylic acid) I is treated with an excess of sodium hydride in dimethylformamide in the presence of an aryl disulfide such as phenyldisulfide at 0° C. to 60° C., according to the general procedure described by Atkinson, et al. in Synthesis, p. 480–481 (1988). The resulting product II is reacted with oxalyl chloride in refluxing chloroform for about 30 minutes to 1 hour to produce the corresponding acid chloride which is then reacted with a primary or secondary amine in chloroform at 0° C. to 20° C. to give the amide III. Alternatively, amide III can be produced directly from II by treatment with BOP reagent (benzotriazol-1-yloxytris-(dimethylamino)phosphonium hexafluorophosphate) in the presence of the desired primary or secondary amine and triethylamine, in a solvent such as dimethylformamide. Other carboxyl group activating reagents such as 1,1'-carbonyldiimidazole can also be used for this step. Saponification of ethyl 5-chloro-3-benzylindole-2-carboxylate (prepared as described below) by methods familiar to those skilled in the art, yields 5-chloro-3-benzylindole-2-carboxylic acid, which can be converted to the desired amides in the manner described for the synthesis of amides III.

The compounds shown in Table II infra, are generally synthesized as in Scheme I, except $R^1OH$ is used in place of $R^2R^3NH$, as depicted in Scheme II below. The substituent groups employed in Scheme II correspond to the substituent groups as defined in Table II, but Scheme II is not limited by the defined substituents or compounds of Table II.

SCHEME II

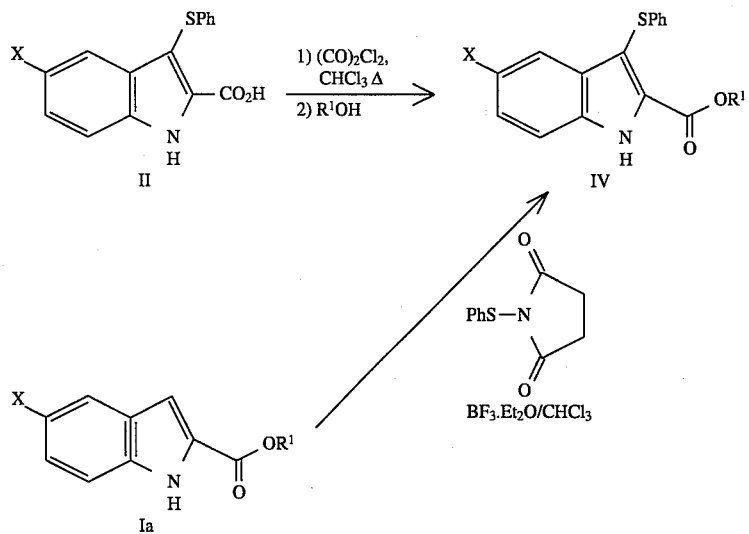

As shown in Scheme II, 3-phenylthioindole-2-carboxylic acid II can be converted to the corresponding acid chloride with oxalyl chloride in refluxing chloroform, and reacted with an alcohol to give the ester IV. In an alternative procedure, Ia may be converted to IV by reaction with N-phenylthiosuccinimide in chloroform at room temperature with a Lewis acid, such as boron trifluoride etherate, as catalyst (as shown in Scheme II). The compound ethyl 5-chloro-3-benzylindole-2-carboxylate was prepared according to the procedure described by Inaba, et al., in Chem. Pharm. Bull., 24, p. 1076–1082 (1976).

Scheme III, below, is a general route for synthesizing, e.g., the compounds shown in Table III, infra. The substituent groups employed in Scheme III correspond to the substituent groups as defined in Table III, but Scheme III is not limited by the defined substituents or compounds of Table III.

IV-A and IV-B, respectively, correspond to the substituent groups as defined in Tables IV-A and IV-B, respectively, but Schemes IV-A and IV-B are not limited by the defined substituents or compounds of Tables IV-A and IV-B.

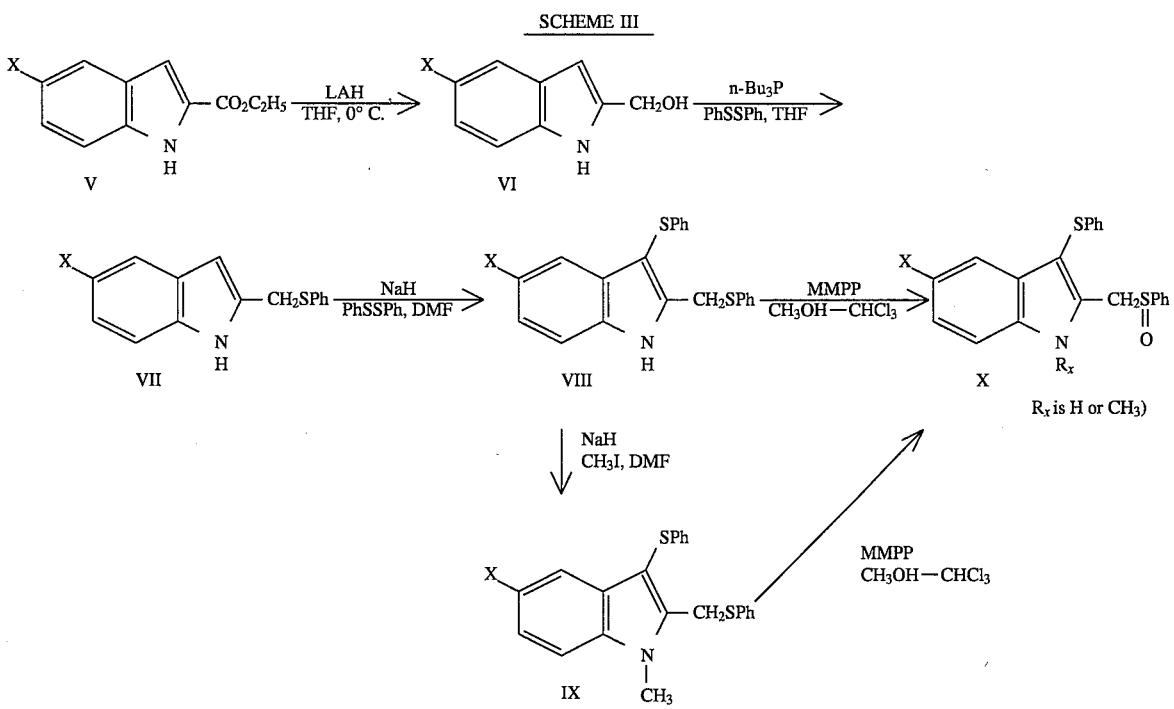

As shown in Scheme III, commercially available ethyl indole-2-carboxylate (compound V wherein X is —H) or ethyl 5-chloroindole-2-carboxylate (compound V wherein X is —Cl), was reduced to the primary alcohol VI with an excess of lithium aluminum hydride in tetrahydrofuran at 0° C. Compound VI was converted to the sulfide VII by treatment with an excess of tri-n-butylphosphine and an aryldisulfide such as phenyldisulfide in tetrahydrofuran at 0° C. to 20° C. for 6–24 hours. Reaction of sulfide VII with sodium hydride, an aryldisulfide such as phenyldisulfide, in dimethylformamide at 0° C. to 20° C. for 1 to 18 hours produces bis-sulfide VIII. Aryl disulfides which were not commercially available were obtained by oxidation of the commercially available aryl mercaptan with dimethyl sulfoxide and iodine, according to the procedure described by Orville G. Lowe in J. Org. Chem., 40, p. 2096–2098 (1975). Compound VIII can be N-alkylated, if desired, by methods familiar to those trained in the art, e.g., by treatment with sodium hydride in dimethylformamide at 0° C. in the presence of an alkylating agent such as iodomethane, to give compound IX. Thereafter, compound VIII (or IX) is treated with one equivalent of peracid such as monoperoxyphthalic acid, magnesium salt (MMPP), or meta-chloroperoxy-benzoic acid in methanol or chloroform-methanol at 0° C. for 30 minutes to 3 hours, to give predominately sulfoxide X.

Schemes IV-A and IV-B, below, show a general route for synthesizing, e.g., the compounds shown in Tables IV-A and IV-B, infra. The substituent groups employed in Schemes

SCHEME IV-A

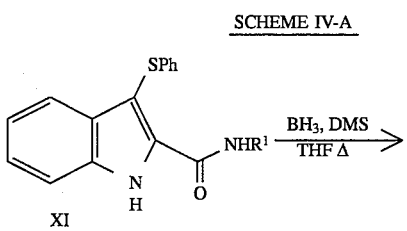

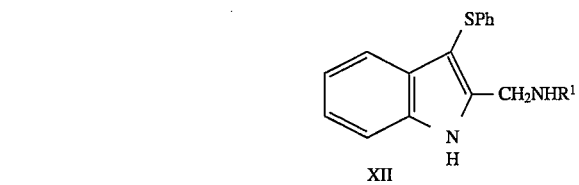

SCHEME IV-B

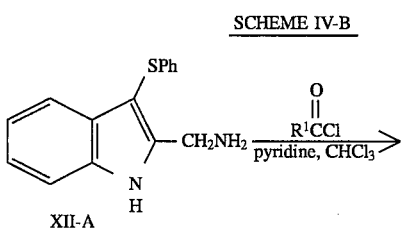

-continued
SCHEME IV-B

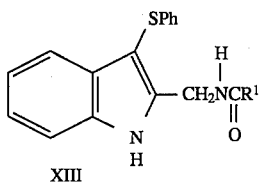

XIII

As shown in Scheme IV-A, 3-phenylthioindole-2-carboxamides XI can be reduced to primary or secondary amines XII by reaction with an excess of borane-dimethylsulfide complex in refluxing tetrahydrofuran for 6–24 hours. As shown in Scheme IV-B, the primary amine XII-A can be acylated with an acid chloride, such as benzoyl chloride, in chloroform in the presence of pyridine, to give the amide XIII.

Scheme V, below, is a general route for synthesizing, e.g., the compounds shown in Table V-A and Table V-B, infra. The substituent groups employed in Scheme V correspond to the substituent groups as defined in Tables V-A and V-B, but Scheme V is not limited by the defined substituents or compounds of Tables V-A and V-B.

be converted to the monoanion with n-butyllithium in tetrahydrofuran at −78° C., and then reacted with carbon dioxide to give carboxylate XVI. The dianion formed by the reaction of XVI with t-butyllithium could be reacted with an isocyanate, such as phenylisocyanate, to give a mixture of monoacylated product and diacylated product XVII (see Table V-B). Alternatively, the dianion formed by the reaction of XVI with t-butyllithium could be reacted with an N-methoxy-N-methyl amide such as N-methoxy-N-methyl-furan-2-carboxamide (prepared in a manner familiar to those skilled in the art, e.g., by the methods described in Scheme 1) to produce ketones XVIII. The methodology described above is essentially that used by A. J. Katritsky and K. Akutagawa to prepare 2-indoleacetic acids, and is published in J. Am. Chem. Soc., 108, 6808 (1986).

Scheme VI, below, is a general route for synthesizing, e.g., the compounds shown in Table VI, infra. The substituent groups employed in Scheme VI correspond to the substituent groups as defined in Table VI, but Scheme VI is not limited by the defined substituents or compounds of Table VI.

SCHEME V

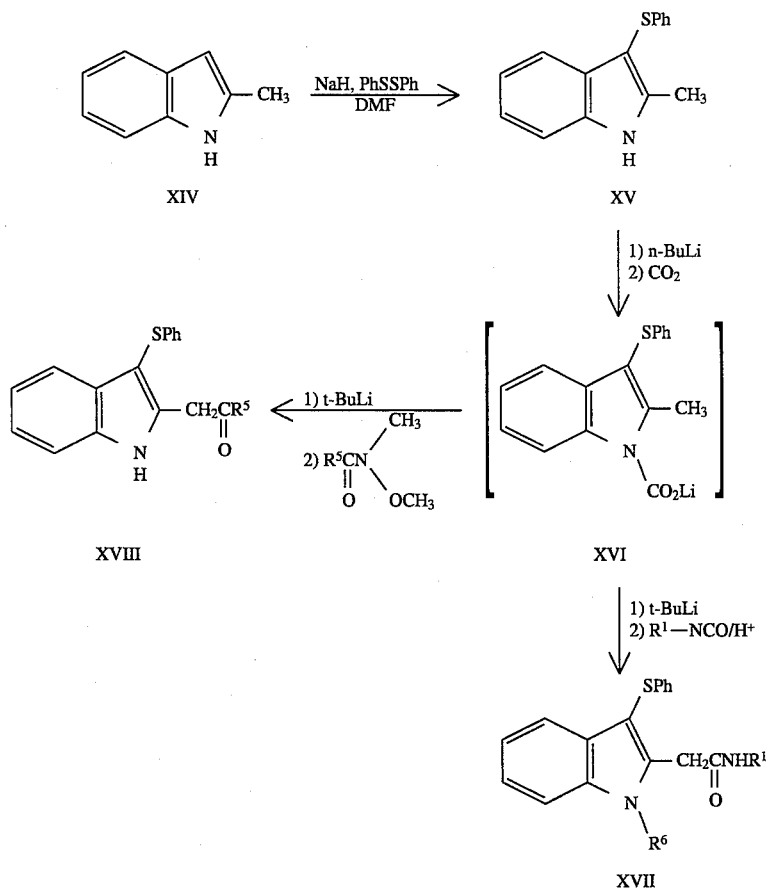

As shown in Scheme V, commercially available 2-methylindole XIV can be treated with sodium hydride in dimethylformamide in the presence of an aryldisulfide such as phenyldisulfide to give compound XV. Compound XV can

SCHEME VI

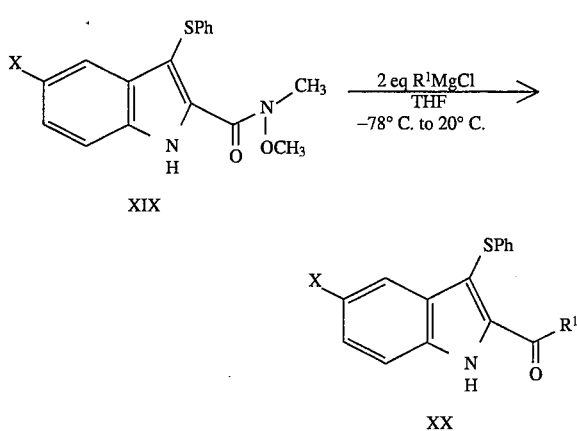

As shown in Scheme VI, N-methoxy-N-methyl-3-phenylthioindole-2-carboxamide XIX (or N-methoxy-N-methyl-5-chloro-3-phenylthioindole-2-carboxamide) (prepared as in Scheme 1) can be reacted with Grignard reagents (wherein $R^1$ is not hydrogen) such as phenylmagnesium chloride, in tetrahyrodrofuran at −78° C. to 20° C. for 18–48 hours, or XIX can be reacted with other organometallic reagents well known in the art to one of ordinary skill, to produce ketones XX.

The compounds shown in Table VII infra, can generally be synthesized by those of ordinary skill in the art according to methods described in Schemes I through VI, with the exception of 2-(2-benzoxazol-2-ylethyl)-3-phenylthioindole (compound XXIV), the synthesis of which is described below in Scheme VII.

ran at 0° C. to 20° C. for 2–4 hours. Aldehyde XXII could be reacted with the lithium salt of [(benzoxal-2-yl)methyl] diethyl-phosphonate to produce olefin XXIII, which is then hydrogenated in the presence of 10% palladium on charcoal in methanol under one atmosphere of hydrogen to give compound XXIV.

The compound 5-chloro-2-cyano-3-phenylthioindole in Table VII can be prepared by dehydro-sulfurization of 5-chloro-3-phenylthioindole-2-thiocarboxamide with, e.g., $Hg(OAc)_2$.

Using methods well-known to those skilled in the art, compounds of formula A where Y is —SO— or —SO$_2$— can be synthesized by treatment of compounds where Y is —S— with a suitable oxidizing agent such as, for example, meta-chloroperoxybenzoic acid (MCPBA), sodium periodate or hydrogen peroxide in an appropriate solvent such as MeOH, $CHCl_3$ or acetic acid, or potassium persulfate in a solvent such as MeOH/$H_2O$.

Alternative routes to amide derivatives of formula A where Y=—SO— or —SO$_2$— are shown in Scheme VIII. Intermediate acid II can be oxidized (with for example meta-chloroperoxybenzoic acid (MCPBA) in $CHCl_3$) to the Y=—SO— or —SO$_2$— acid derivative XXV which can then be converted to the corresponding amide derivatives XXVII employing the amide forming conditions indicated in Scheme I. In another useful sequence, intermediate ester IVa can be oxidized to the Y=—SO— or —SO$_2$— ester intermediate XXVI which on reaction with ammonia or a primary amine with heating is converted to compounds of formula XXVII.

SCHEME VII

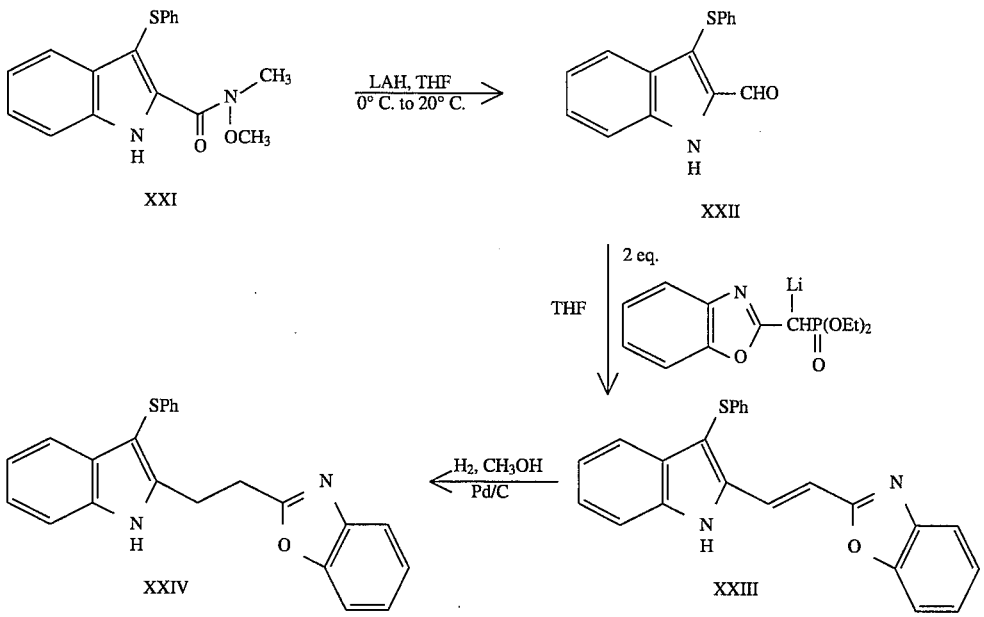

As shown in Scheme VII, N-methoxy-N-methyl-3-phenylthioindole-2-carboxamide XXI can be reduced to aldehyde XXII with lithium aluminum hydride in tetrahydrofu-

SCHEME VIII
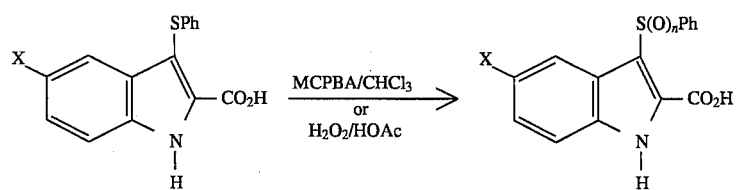
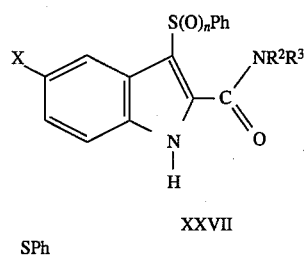
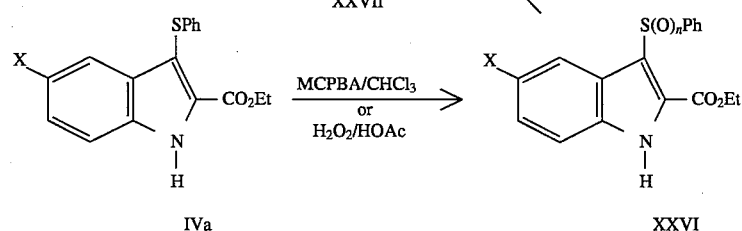

TABLE I

[Structure: X-substituted indole with Y-Ph at position 3, and C(=O)-N(R²)(R³) at position 2, NH on indole]

| X | Y | R² | R³ | mp. |
|---|---|---|---|---|
| H | S | CH₃ | CH₃ | 194–195° C. |
| H | S | H | CH₂Ph | 179–181° C. |
| H | S | H | Ph | 194–196° C. |
| H | S | H | n-C₄H₉ | 161–163° C. |
| H | S | H | CH₂CH₂Ph | 147–149° C. |
| Cl | S | CH₃ | OCH₃ | 57–59° C. |
| Cl | S | H | 2-pyridyl | 255–256° C. |
| H | S | H | CH₃ | 197–199° C. |
| Cl | S | H | nC₃H₇ | 210–212° C. |
| Cl | S | H | —CH₂-(2-pyridyl) | 240–241° C. |
| Cl | S | H | cyclohexyl | 255–256° C. |
| F | S | H | 2-pyridyl | 239–241° C. |
| Cl | S | H | 3-hydroxyphenyl | 232–233° C. |
| Cl | CH₂ | H | —CH₂-(2-pyridyl) | 243–244° C. |
| Cl | S | H | 3-methoxyphenyl | 221° C. |
| Cl | S | H | —CH₂-(2-furyl) | 214° C. |
| Cl | S | H | —CH₂CH₂CH₂OH | 215° C. |
| Cl | S | H | 4-methoxyphenyl | 229° C. |
| Cl | S | H | CH₃ | 220–221° C. |
| Cl | S | H | CH₂CH₂CH₂OCH₃ | 170–171° C. |

TABLE I-continued

Structure: 5-X-3-(Y-Ph)-indole-2-carboxamide N(R²)(R³)

| X | Y | R² | R³ | mp. |
|---|---|---|---|---|
| Cl | S | H | CH₂-(2,3-dimethoxyphenyl) | 184° C. |
| Cl | S | H | CH₂-(1H-benzimidazol-2-yl) | 259–260° C. (HCl salt) |
| Cl | S | H | CH₂CH₂-(imidazol-1-yl) | 256° C. (HCl salt) |
| Cl | S | H | CH(CH₃)₂ | 193–194° C. |
| Cl | S | CH₃ | Ph | 191–192° C. |
| Cl | S | H | CH₂CH₂CH₂N(CH₃)₂ | 229–230° C. (HCl salt) |
| Cl | S | H | C₂H₅ | 210–211° C. |
| Cl | S | H | Ph | 245–246° C. |
| Cl | S | H | CH₂-(3-methoxyphenyl) | 172° C. |
| Cl | S | H | CH₂CH₂CH₂-morpholino | 162–164° C. |
| Cl | S | H | CH₂-cyclopropyl | 219–219.5° C. |
| Cl | S | H | CH₂Ph | 222° C. |
| Cl | S | H | CH₂-(4-methoxyphenyl) | 198° C. |
| Cl | S | H | CH₂CH₂OCH₂CH₂OH | 161.5–162.5° C. |
| Cl | S | H | 4-hydroxyphenyl | >300° C. |
| Cl | S | H | CH₂CH₂OCH₃ | 216–217.5° C. |
| Cl | S | H | CH₂CH₂OC₂H₅ | 165.5–167° C. |
| Cl | S | H | CH₂-(tetrahydrofuran-2-yl) | 182–183° C. |

TABLE I-continued
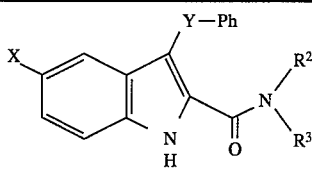
| X | Y | R² | R³ | mp. |
|---|---|---|---|---|
| Cl | S | H | 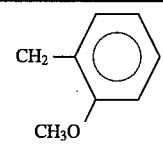 | 201° C. |
| Cl | S | H | CH₂CHCH₃<br>\|<br>OH | 205° C. |
| Cl | S | H | 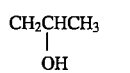 | 228–229° C. |
| Cl | S | H | CH₂CH₂OH | 222–223.5° C. |
| Cl | S | H | 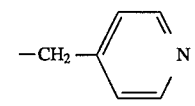 | 151–152° C. |
| Cl | S | H | OCH₃ | 179–180° C. |
| Cl | S | H | —CH—CH₂CH₃<br>\|<br>CH₂OH | 153–154° C. |
| Cl | S | H | O<br>\|\|<br>CH₂COC₂H₅ | 215–215.2° C. |
| Cl | S | H | —CHCH₂OCH₃<br>\|<br>CH₃ | 168–169° C. |
| Cl | S | H | 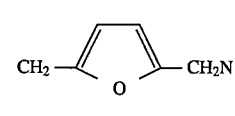 | 202–203° C. |
| Cl | S | H | 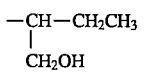 | 209–210° C. |
| Cl | S | H | 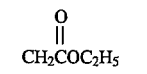 ·HCl | 188–189° C. |
| Cl | S | H | 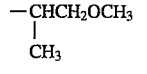 | 205–206° C. |
| Cl | S | H | —CHCH₂CH₃<br>▲<br>CH₂OH | 138–139° C. |
| Cl | S | H | —CHCH₂CH₃<br>⋮<br>CH₂OH | 137.5–139° C. |
| Cl | S | H | OH<br>\|<br>—CH₂CHCH₂OH | 219–221° C. |

TABLE I-continued
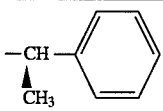
| X | Y | R² | R³ | mp. |
|---|---|---|---|---|
| Cl | S | H | -CH(CH₃)-Ph (wedge) | 208–210° C. |
| Cl | S | H | -CH(CH₂OH)-Ph (dashed) | 223–226° C. |
| Cl | S | H | -CH(CH₂OH)-Ph (wedge) | 223–226° C. |
| Cl | S | H | -CH(CH₃)-Ph (dashed) | 208–210° C. |
| Cl | S | H | -CH₂-(2-methoxypyridin-4-yl) | 227–228° C. |
| Cl | S | H | -CH₂-(3-hydroxymethylphenyl) | 229–230° C. |
| Cl | S | H | -CH₂-(2-(2-hydroxyethyl)phenyl) | 217–219° C. |
| Cl | S | H | -CH₂-(3-hydroxyphenyl) | 214–216° C. |
| Cl | S | H | -CH₂-CH(OH)-Ph | 193–195.5° C. |
| Cl | S | H | —H | 213–215° C. |
| Cl | SO₂ | H | H | 255–257° C. |
| Cl | SO₂ | H | -CH₂-Ph | 249–251° C. |
| Cl | SO₂ | H | -CH₂CH₂OH | 198–200° C. |

TABLE I-continued

[Structure: X-substituted indole with Y-Ph at 3-position and C(=O)NR²R³ at 2-position]

| X | Y | R² | R³ | mp. |
|---|---|----|----|-----|
| Cl | SO₂ | H | —CH₂-(2-methoxy-pyridin-4-yl) | |
| Cl | SO₂ | H | —CH₂-(furan-2-yl) | 212–215° C. |
| Cl | SO₂ | H | —CH₂-(2-methyl-thiazol-4-yl) | 211–215° C. |
| Cl | SO₂ | H | —CH₂-(4-fluorophenyl) | 275–278° C. |
| Cl | SO₂ | H | —CH₂-(2,3-dichlorophenyl) | 265–270° C. |
| Cl | SO₂ | H | (R)-CH(CH₃)Ph | 149° C. |
| Cl | SO₂ | H | (S)-CH(CH₃)Ph | 175° C. |
| Cl | SO₂ | H | —CH₂-(pyridin-4-yl) | 278–281° C. |

TABLE II

[Structure: X-substituted indole with Y-R at 3-position and C(=O)OR^{1b} at 2-position]

| X | Y | R | R^{1b} | mp | X | Y | R | R^{1b} | mp |
|---|---|---|--------|-----|---|---|---|--------|-----|
| H | S | Ph | CH₃ | 179–180° C. | OCH₃ | S | Ph | CH₃ | 211–212° C. |
| H | S | 2-methoxyphenyl | CH₃ | 195–197° C. | Cl | S | Ph | CH₃ | 193–196° C. |
| | | | | | Cl | S | Ph | CH₂Ph | 154–155° C. |
| | | | | | Cl | S | Ph | C₂H₅ | 163–164° C. |
| | | | | | Cl | CH₂ | Ph | C₂H₅ | 196–197° C. |
| | | | | | F | S | Ph | C₂H₅ | 149° C. |

TABLE III

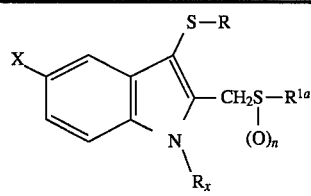

| X | R | R¹ᵃ | n | $R_x$ | mp |
|---|---|---|---|---|---|
| H | Ph | Ph | 1 | H | 71–74° C. |
| H | Ph | Ph | 0 | H | — |
| H | Ph | Ph | 2 | H | 168–169° C. |
| H | 3-CH₃-C₆H₄ | Ph | 1 | H | 166–167° C. |
| H | 4-CH₃-C₆H₄ | Ph | 1 | H | 164.5–166.5° C. |
| OCH₃ | Ph | Ph | 1 | H | 70–80° C. |
| H | 2-CH₃-C₆H₄ | Ph | 1 | H | 171.5–172.5° C. |
| H | Ph | Ph | 0 | CH₃ | 98–99° C. |
| H | Ph | Ph | 1 | CH₃ | 177–178° C. |
| H | Ph | 4-OCH₃-C₆H₄ | 1 | H | — |
| H | Ph | CH₃ | 1 | H | 164–168° C. |
| H | Ph | 3-CH₃-C₆H₄ | 0 | H | — |
| H | Ph | 3,5-(CH₃)₂-C₆H₃ | 0 | H | — |
| H | Ph | 3,5-(CH₃)₂-C₆H₃ | 1 | H | — |
| H | Ph | 2-CH₃-C₆H₄ | 1 | H | — |
| H | Ph | 2-naphthyl | 1 | H | — |
| H | Ph | 2,4-(OCH₃)₂-C₆H₃ | 1 | H | — |
| H | Ph | 2-OCH₃-C₆H₄ | 1 | H | 138–140° C. |
| H | Ph | 4-OH-C₆H₄ | 0 | H | — |

TABLE III-continued

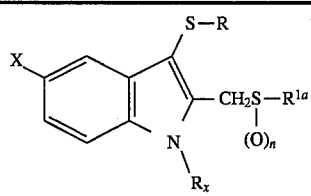

| X | R | R¹ᵃ | n | $R_x$ | mp |
|---|---|---|---|---|---|
| H | Ph | 4-OH-C₆H₄ | 1 | H | 219–220° C. |
| Cl | Ph | Ph | 1 | H | 158–162° C. |
| H | Ph | 3-OH-C₆H₄ | 1 | H | — |

TABLE IV-A

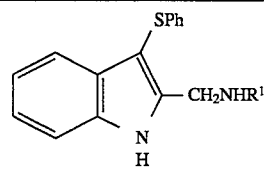

| R¹ | m.p. |
|---|---|
| —CH₂Ph | 199–201° C. |
| —Ph | 167–170° C. |
| —n-C₄H₉ | 177–179° C. |
| —H | — |

TABLE IV-B

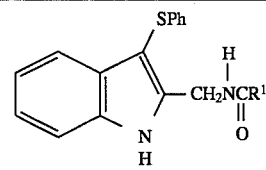

| R¹ | m.p. |
|---|---|
| —CH₃ | — |
| —Ph | 64–65° C. |

TABLE V-A

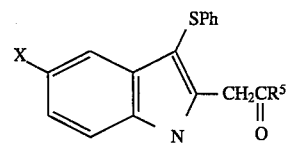

| X | R⁵ | R⁶ | mp |
|---|---|---|---|
| H | —CH₂Ph | H | — |
| H | —Ph | H | 154–155° C. |

TABLE V-A-continued

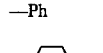

| X | R⁵ | R⁶ | mp |
|---|---|---|---|
| H | —CH₃ | H | 101.5–103.5° C. |
| H | (benzyl-pyridyl) | H | 87–90° C. |
| H | (furyl) | H | 127–129° C. |
| Cl | —OC₂H₅ | H | 99–103° C. |

TABLE V-B

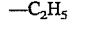

| X | R¹ | R⁶ | mp |
|---|---|---|---|
| H | —Ph | H | 66–68° C. |
| H | —Ph | —CNHPh<br>‖<br>O | 123–125° C. |

TABLE VI

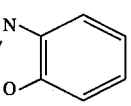

| X | Y | R¹ᵃ | mp |
|---|---|---|---|
| Cl | S | —Ph | 154–155° C. |
| Cl | S | —CH₂Ph | 219–220° C. |
| H | S | —Ph | 121.5–123° C. |
| H | S | —C₆H₄Cl | 142–149° C. |
| Cl | S | —C₂H₅ | 196–197° C. |
| Cl | S | —C₆H₄Cl | 214–215° C. |
| Cl | S | —CH₃ | 178° C. |
| Cl | CH₂ | —C₂H₅ | 203–205° C. |
| Cl | CH₂ | —Ph | 161–163° C. |
| Cl | SO₂ | cyclopropyl | 224–226° C. |
| Cl | SO₂ | —C₂H₅ | 226–227° C. |

TABLE VI-continued

| X | Y | R¹ᵃ | mp |
|---|---|---|---|
| Cl | SO₂ | —CH₃ | 184–187.5° C. |

TABLE VII

| X | Rₓ | R⁶ | mp |
|---|---|---|---|
| H | —CH₃ | H | 128–130° C. |
| H | —CH₃ | —CNHPh<br>‖<br>O | 157–159° C. |
| H | —CH₃ | —CPh<br>‖<br>O | 124–125° C. |
| H | —CH₂CH₂Ph | H | 117–120.5° C. |
| H | —CH₂CH₂-(benzoxazolyl) | H | 192–193° C. |
| Cl | —CN | H | 172–174° C. |
| Cl | —C(=S)—NHCH₂-(furyl) | H | 143–144° C. |
| Cl | —C(=S)—NH₂ | H | 217 (decomp.) |

The compounds of the present invention are useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

The compounds of this invention are also useful in the preparation and execution of screening for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase e.g., by competitive inhibition. Thus the compounds of this invention are commercial products to be sold for these purposes.

For inhibition of HIV reverse transcriptase, the prevention or treatment of infection by HIV and the treatment of AIDS or ARC, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV reverse transcriptase inhibitor compounds with one or more agents useful in the treatment of AIDS. The compounds of this invention can be administered in combination with other compounds that are HIV reverse transcriptase inhibitors, and/or with compounds that are HIV protease inhibitors. For example, the compounds of this invention may be effectively administered, whether at periods of pre-exposure and/or post-exposure, in combination with effective amounts of the AIDS antivitals, such as those in the following Table VIII.

When used in a combination treatment with compounds of the instant invention, dosage levels of HIV protease inhibitors of the order of 0.02 to 5.0 or 10.0 grams-per-day are useful in the treatment or prevention of the above-indicated conditions, with oral doses two-to-five time higher. For example, infection by HIV is effectively treated by the administration of from 10 to 50 milligrams of the HIV protease inhibitor per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Dosages of HIV reverse transcriptase inhibitors, when used in a combination treatment with compounds of the instant invention, are comparable to those dosages specified above for the instant compounds.

It will be understood that the scope of combinations of the compounds of this invention with AIDS antivitals is not limited by Table VIII but includes in principle any combination with any pharmaceutical composition useful for the treatment of AIDS.

TABLE VIII

| Drug Name | Manufacturer | Indication |
| --- | --- | --- |
| ddI Dideoxyinosine | Bristol-Myers (New York, NY) | AIDS, ARC |
| Dideoxycytidine; ddC | Hoffman-La Roche (Nutley, NJ) | AIDS, ARC |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| L-697,661 | Merck (Rahway, NJ) | AIDS, ARC, asymptomatic HIV positive, also in combination with AZT. |
| L-696,229 | Merck (Rahway, NJ) | AIDS, ARC, asymptomatic HIV positive, also in combination with AZT. |
| L-735,524 | Merck (Rahway, NJ) | AIDS, ARC, asymptomatic HIV positive, also in |

TABLE VIII-continued

| Drug Name | Manufacturer | Indication |
|---|---|---|
| | | combination with AZT. |
| L-738,372 | Merck (Rahway, NJ) | AIDS, ARC, asymptomatic HIV positive, also in combination with AZT. |
| L-738,872 | Merck (Rahway, NJ) | AIDS, ARC, asymptomatic HIV positive, also in combination with AZT. | compounds of Table VIII are the following:

L-697,661 is 3-([(4,7-dichloro-1,3-benzoxazol-2-yl)-methyl]-amino)-5-ethyl-6-methyl-pyridin-2(1H)-one;

L-696,229 is 3-[2-(1,3-benzoxazol-2-yl)ethyl]-5-ethyl-6-methyl-pyridin-2(1H)-one; L-735,524 is an HIV protease inhibitor with the chemical name N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)piperazinyl))pentaneamide;

L-738,372 is 6-chloro-4(S)-cyclopropyl-3,4-dihydro-4-((2-pyridyl)-ethynyl)-quinazolin-2(1H)-one; L-738, 872 is N-tert-butyl-1-[2'-(R)-hydroxy-4'-phenyl-3'(S)-[3"(R)-[1'",1'"-dioxo-2'"(R)-methylethyl] tetrahydrothienyloxycarbonylamino]-butyl]-4-[4'-(2"-chloro-6"-methyl)pyridylmethyl]-piperazine-2(S)-carboxamide.

REVERSE TRANSCRIPTASE ASSAY

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C).oligo $d(G)_{12-18}$. The inhibitors of the present invention inhibit this incorporation.

Thirty uL of a reaction mixture containing equal volumes of: 500 mM Trise.HCl (pH 8.2), 300 mM $MgCl_2$, 1200 mM KCl, 10 mM DTT, 400 µg/mL poly r(c).oligo d(G) [prepared by dissolving 1.5 mg (25 U) poly r(C).oligo d(G) in 1.5 ml sterile distilled $H_2O$ and diluting to 400 µg/ml], 0.1 µCi/µl [$^3$H] dGTP, 160 µM dGTP, was added to 10 µl sterile distilled $H_2O$, 2.5 µl of potential inhibitor and 10 µL of 5 nM purified HIV $RT_R$ in tubes. The mixture was incubated at 37° C. for 45 minutes.

After incubation is complete, the tubes were cooled in ice for 5 minutes. Ice-cold 13% TCA containing 10 mM $NaPP_i$ (200 µl) are added and the mixture incubated on ice for 30 minutes. The precipitated cDNA is removed by filtration using presoaked glass filters [TCA, $NaPP_i$]. The precipitate is then washed with 1N HCl, 10 mM $NaPP_i$.

The filter discs are then counted in a scintillation counter.

Under these conditions [dGTP] and poly r(C).oligo $d(G)_{12-18}$ each are approximately equal to the appropriate Km value. Approximately 5–6,000 cpm of [$^3$H] dGMP are incorporated into acid-precipitable material. The RT reaction is concentration- and time-dependent. DMSO (up to 5%) does not affect enzyme activity. Calculated $IC_{50}$ values for the tested compounds of this invention vary from about 3 nM to more than 300 µM. The $IC_{50}$ values of the most preferred compounds range from about 3 nM to about 35 nM.

INHIBITION OF VIRUS SPREAD

A. Preparation of HIV-infected MT-4 Cell Suspension

MT cells were infected at Day 0 at a concentration of 250,000 per ml with a 1:2000 dilution of HIV-1 strain IIIb stock (final 125 pg p24/ml; sufficient to yield ≦1% infected cells on day 1 and 25–100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% $CO_2$ atmosphere.

B. Treatment with Inhibitors

Serial two-fold dilutions of compound were prepared in cell culture medium. At Day 1, aliquots of 125 µl of compound were added to equal volumes of HIV-infected MT-4 cells (50,000 per well) in a 96-well microtiter cell culture plate. Incubation was continued for 3 days at 37° C. in 5% $CO_2$ atmosphere.

C. Measurement Of Virus Spread

Using a multichannel pipettor, the settled cells were resuspended and a 125 µl harvested into a separate microtiter plate. After the settling of the cells, the plates were frozen for subsequent assay of the supernatant for HIV p24 antigen.

The concentration of HIV p24 antigen was measured by an enzyme immunoassay, described as follows. Aliquots of p24 antigen to be measured were added to microwells coated with a monoclonal antibody specific for HIV core antigen. The microwells were washed at this point, and at other appropriate steps that follow. Biotinylated HIV-specific antibody was then added, followed by conjugated streptavidin-horseradish peroxidase. A color reaction occurs from the added hydrogen peroxide and tetramethylbenzidine substrate. Color intensity is proportional to the concentration of HIV p24 antigen.

The cell culture inhibitory concentration ($ClC_{95}$) for each compound is defined as that concentration which inhibited by greater than 95% the spread of infection, as assessed by a greater than 95% reduction in p24 antigen production relative to untreated controls. The tested compounds of the present invention were found to have $CIC_{95}$ values ranging from about 3 nM to about 400 nM for preferred species, and up to about 40 µM for others.

EXAMPLE 1

Preparation of N-(3-pyridylmethyl)-5-chloro-3-phenylthioindole-2-carboxamide

Step A: 5-Chloro-3-phenylthioindole-2-carboxylic acid

To a suspension of sodium hydride (3.0 g, 60% dispersion in oil, 0.076 mol) in dimethylformamide (125 mL) was added 5-chloroindole-2-carboxylic acid (5.0 g, 0.0255 mol) and phenyldisulfide (6.1 g, 0.028 mol). The reaction was heated under nitrogen at 50° C. overnight. The reaction was cooled, and additional sodium hydride (1.8 g) and phenyldisulfide (3.6 g) were added and heating continued for 1 h. The reaction was cooled and the dimethylformamide distilled in vacuo. The residue was partitioned between ethyl acetate and water. The aqueous layer was separated and the pH adjusted to pH1 with 10% aqueous hydrochloric acid. The aqueous phase was extracted with ethyl acetate, and the ethyl acetate extract was washed with water and saturated brine, and dried over magnesium sulfate. The crude product was recrystallized from ethyl acetate in hexane to afford the title compound as an off-white solid.

Step B: N-(3-pyridylmethyl)-5-chloro-3-phenylthioindole-2-carboxamide

Benzotriazol-1-yloxytris(dimethylamino)phosphonium hexafluorphosphate (0.73 g, 1.6 mmol) was added to a solution of 5-chloro-3-phenylthio-indole-2-carboxylic acid (0.50 g, 1.6 mmol), 3-aminomethylpyridine (0.35 g, 3.2 mmol) and triethylamine (0.50 mL, 3.2 mmol) in degassed dimethylformamide (25 mL). The reaction was stirred at room temperature overnight. The precipitated product was filtered and the filter cake washed well with water. The solid was triturated with 30% ethyl acetate in hexane, filtered and dried at 60° C. in vacuo for 72 h. The title compound was obtained as an off-white solid, mp 240°–241° C. Anal. Calc. for $C_{21}H_{16}ClN_3OS \cdot 0.25 H_2O$: C, 63.31; H, 4.17; N, 10.54. Found: C, 63.34; H, 4.06; N, 10.71. NMR (DMSO-$d_6$): δ12.54 (1H, s), 8.91 (1H, t, J=6 Hz), 8.51 (1H, s), 8.42 (1H, d, J=5 Hz), 7.58 (2H, m), 7.45 (1H, m), 7.25 (4H, m), 7.15 (1H, t, J=7 Hz), 7.04 (2H, d, J=8 Hz), 4.58 (2H, d, J=6 Hz).

EXAMPLE 2

Preparation of Methyl 5-chloro-3-phenylthioindole-2-carboxylate

Oxalyl chloride (0.70 mL, 9.6 mmol) was added to a solution of 5-chloro-3-phenylthioindole-2-carboxylic acid (0.97 g, 3.2 mmol) in chloroform (50 mL) under nitrogen. The reaction was refluxed for 3 h, cooled and reduced to dryness in vacuo. The resulting solid was dissolved in chloroform and added to methanol at 0° C. The methanol was removed in vacuo and the crude product chromatographed on silica gel with 20% ethyl acetate in hexane. The title compound was obtained as a solid, mp 193°–196° C. Anal. Calc. for $C_{16}H_{12}ClNO_2S$: C, 60.47; H, 3.81; N, 4.42. Found: C, 60.09; H, 3.50; N, 4.67.

EXAMPLE 3

Preparation of Ethyl 5-chloro-3-benzylindole-2-carboxylate

The title compound was prepared according to the procedure described by Inaba, S., et al., Chem. Pharm. Bull., 24, 1076–1082 (1976). Recrystallization from benzene gave the title compound as pale yellow needles, mp196°–197° C. Anal. Calc. for $C_{18}H_{16}ClNO_2$: C, 68.90; H, 5.13; N, 4.46. Found: C, 68.64; H, 5.10; N, 4.56.

EXAMPLE 4

Preparation of 2-Phenylsulfinylmethyl-3-phenylthioindole

Step A: 2-Hydroxymethylindole

A suspension of lithium aluminum hydride (2.0 g, 0.20 mol) in tetrahydrofuran (100 mL) was cooled with stirring to 0° C. under nitrogen. A solution of ethyl indole-2-carboxylate (10.0 g, 0.052 mol) in tetrahydrofuran was added dropwise, maintaining the reaction temperature between 0°–5° C. After 1 h, the reaction was quenched with saturated sodium potassium tartrate solution. The reaction was filtered and the filter cake washed well with tetrahydrofuran. The tetrahydrofuran was evaporated in vacuo and the residue partitioned between ethyl acetate and water. The ethyl acetate solution was washed with water, saturated brine, dried over magnesium sulfate, filtered and freed of solvent. The title compound was obtained as a yellowish solid. NMR (CDCl$_3$): δ8.18 (1H, bs), 7.57 (1H, d, J=8 Hz), 7.35 (1H, d, J=8 Hz), 7.26 (1H, s), 7.18 (1H, dt, J=1, 8 Hz), 7.10 (1H, dt, J=1, 8 Hz), 6.41 (1H, bs), 4.84 (2H, s).

Step B: 2-Phenylthiomethylindole

2-Hydroxymethylindole (6.94 g, 0.047 mol) and phenyldisulfide (10.8 g, 0.049 mol) were dissolved in tetrahydrofuran (200 mL) and cooled to 0° C. under nitrogen. Tri-n-butylphosphine (11.7 mL, 0.047 mol) was added and the reaction stirred for 1 h. Additional phenyldisulfide (1.5 g, 0.007) and tri-n-butylphosphine (5.1 mL, 0.20 mol) was added, and the reaction stirred at room temperature until complete. The tetrahydrofuran was removed in vacuo and the residue chromatographed on silica gel eluting with 5% ethyl acetate in hexane. The title compound was obtained as clear colorless plates, mp 100°–101.5° C. Anal. Calc. for $C_{15}H_{13}NS$: C, 75.27, H, 5.47, N, 5.85. Found: C, 74.52, H, 5.39, N, 5.95.

Step C: 3-Phenylthio-2-phenylthiomethylindole

A suspension of sodium hydride (0.37 g 60% dispersion in oil, 9.4 mmol) in dimethylformamide (50 mL) was cooled to 0° C. 2-Phenylthiomethylindole (1.5 g, 6.3 mmol) was added portionwise, and the reaction stirred at 0° C. for 15 min. Phenyldisulfide (1.5 g, 6.9 mmol) was added and the reaction stirred at 20° C. for 6 h. The reaction was quenched with water and extracted with ethyl acetate. The organic extract was washed with water, saturated brine and dried over magnesium sulfate. Filtration and evaporation of solvent left an oil which was purified by medium pressure chromatography on silica gel using 5% ethyl acetate in hexane. The title compound was obtained as an oil. Anal. Calc. for $C_{21}H_{17}NS_2 \cdot H_2O \cdot 0.15 C_4H_8O_2$: C, 68.50; H, 5.33; N 3.60. Found: C, 68.40; H, 4.65; N, 3.86.

Step D: 2-Phenylsulfinylmethyl-3-phenylthioindole

A solution of 3-phenylthio-2-phenylthiomethylindole (0.750 g, 2.94 mmol) in methanol (100 mL) was cooled to 0° C. with stirring. Monoperoxyphthalic acid magnesium salt (0.908 g, 80% peracid) in methanol (50 mL) was added slowly dropwise. After addition, the reaction was stirred an additional 30 min., then quenched with 10% aqueous sodium thiosulfate (2 mL). The methanol was removed in vacuo, and the residue partitioned between ethyl acetate and water. The organic phase was washed successively with water and saturated brine, then dried over magnesium sulfate. Filtration and concentration of the filtrate in vacuo gave an oil which was purified by chromatography on silica gel using 20–30% ethyl acetate in hexane. The title compound was obtained as a foam, mp 71°–74° C. Exact mass calculated for $C_{21}H_{17}NOS_2$: 364.082982. Found: 364.084549. NMR (DMSO-$d_6$) δ11.82 (1H, s), 7.50 (6H, m), 7.23 (1H, d, J=8 Hz), 7.15 (3 H, m) 7.05 (2H, m) 6.90 2H, m), 4.43 (1, d, J=13 Hz), 4.38 (1H, d, J=13 Hz).

EXAMPLE 5

Preparation of 2-Phenylcarboxamidomethyl-3-phenylthioindole

Step A: 3-Phenythioindole-2-carboxamide

The title compound was prepared from 3-phenylthioindole-2-carboxylic acid (prepared according to the procedure described by Atkinson, J. G. et al., Synthesis, p. 480–481 (1988), (4.01 g, 0.015 mol), ammonia (large excess), and benzotriazol-1-yloxytris(dimethylamino)phosphonium hexafluorphosphate (7.2 g, 0.016 mol) in dimethylformamide according to the general procedure described in Example 1 for the preparation of N-(3-pyridylmethyl)-5-chloro-3-phenylthio-2-carboxamide. The title compound was obtained as a pale yellow solid.

Step B: 2-Aminomethyl-3-phenylthioindole

A solution of 3-phenylthioindole-2-carboxamide (1.9 g, 7.1 mmol) in tetrahydrofuran was cooled under nitrogen to 0° C. and treated with neat boranedimethylsulfide complex (7.1 mL, 0.070 mol). The reaction was refluxed for 7 h, cooled to 0° C. and quenched with 10% aqueous hydrochloric acid. The solution was adjusted to pH 8 with 20% aqueous sodium hydroxide. The reaction was extracted with ethyl acetate and the organic extract washed with saturated brine, and dried over magnesium sulfate. The title compound was obtained as a pale yellow oil.

Step C: 2-Phenylcarboxamidomethyl-3-phenylthioindole

2-Aminomethyl-3-phenylthioindole (0.85 g, 3.3 mmol) was dissolved in chloroform (15 mL) and cooled under nitrogen to 0° C. Pyridine (2.7 mL, 33 mmol) was added, followed by benzoyl chloride (1.1 mL, 10 mmol). The reaction was stirred at 20° C. for 1 h and 10% aqueous hydrochloric acid added. The layers were separated and the organic phase washed successively with water, saturated sodium bicarbonate and saturated brine. The chloroform solution was dried over magnesium sulfate, filtered and evaporated to dryness. The resulting oil was chromatographed on silica gel with 5% ethyl acetate in methylene chloride. The title compound was obtained as a solid, mp 64°–65° C. Anal. Calc. for $C_{22}H_{18}N_2OS.0.2\ H_2O$: C, 73.00; H, 5.08; N, 7.74. Found: C, 72.93; H, 5.02; N, 7.66.

EXAMPLE 6

Preparation of 2-(N-Phenylacetamido)-3-phenylthioindole and 2-(N-Phenylacetamido)-1-(phenylcarbamoyl-3-phenylthioindole 2-Methyl-3-phenylthioindole (0.50 g, 2.1 mmol) (prepared according to the procedure described by Atkinson, J. G., et al., Synthesis, p. 480–481 (1988), was dissolved in dry tetrahydrofuran and cooled under nitrogen to −78° C. A solution of n-butyllithium in hexane (0.83 mL, 2.5M) was added via syringe. Carbon dioxide was bubbled into the reaction mixture over a period of several minutes; unreacted carbon dioxide was removed by freezing the reaction at liquid nitrogen temperature under high vacuum and warming to −78° C. A solution of t-butyllithium in hexane was added (1.35 mL, 1.7M) and the reaction stirred for 20 min. Phenylisocyanate (0.23 mL, 2.1 mmol) in tetrahydrofuran (1.5 mL) was added and the reaction stirred at 20° C. overnight. The reaction was diluted with water and extracted with ethyl acetate. The organic phase was washed with saturated brine and dried over magnesium sulfate. Filtration and evaporation of solvent left an amber oil. The crude products were chromatographed on silica gel eluting successively with 15%, 20%, and 40% ether in hexane. 2-(N-Phenylacetamido)-3-phenylthioindole was isolated as a solid, mp 66°–68° C. Anal. Calc. for $C_{22}H_{18}N_2OS$: C, 72.98; H, 5.01; N, 7.73. Found: C, 72.99; H, 4.87; N, 7.52. Later fractions contained 2-(N-phenylacetamido)-1-(phenylcarbamoyl)-3-phenylthioindole, mp 123°–125° C. Anal. Calc. for $C_{29}H_{23}N_3O_2S$: C, 70.28, H, 4.67, N, 8.47. Found: C, 70.37, H, 4.61; N, 8.34.

EXAMPLE 7

Preparation of 2-(2-Oxo-2-furan-3-yl)ethyl-3-phenylthioindole

Step A: N-Methoxy-N-methylfuran-3-carboxamide

The title compound was prepared from furan-3-carboxylic acid (3.4 g, 0.030 mol), N,O-dimethylhydroxylamine hydrochloride hydrochloride (2.9 g, 0.030 mol) triethylamine (8.3 mL, 0.060 mol) and benzotriazol-1-yloxytris-(dimethylamino)phosphonium hexafluorphosphate (13.3 g, 0.030 mol) according to the general procedure described in Example 1 for N-(3-pyridylmethyl)-5-chloro-3-phenylthio-2-carboxamide. NMR (DMSO-$d_6$) δ8.25 (1H, s), 7.75 (1H, s), 3.70 (3H, s), 3.22 (3H, s).

Step B: 2-(2-Oxo-2-furan-3-yl)ethyl-3-phenylthioindole

The title compound was prepared from N-methoxy-N-methylfuran-3-carboxamide (0.32 g, 2.1 mmol), and 2-methyl-3-phenylthioindole (0.50 g, 2.1 mmol) according to the general procedure described Example 6 for the preparation of 2-(N-phenylacetamido)-3-phenyl-thioindole. The crude product was chromatographed on silica gel with chloroform. The title compound was obtained as a pale yellow solid, mp 127°–129° C. Anal. Calc. for $C_{20}H_{15}NO_2S$: C, 72.05; H, 4.54; N, 4.20. Found: C, 72.08; H, 4.57; N, 4.24.

EXAMPLE 8

Preparation of 2-Benzoly-5-chloro-3-phenylthioindole

Step A: N-Methoxy-N-methyl-5-chloro-3-phenylthioindole-2-carboxamide

The title compound was prepared from 5-chloro-3-phenylthioindole-2-carboxylic acid (1.0 g, 3.30 mmol)) N,O-dimethylhydroxylamine hydrochloride (0.64 g, 6.6 mmol), triethylamine (1.0 mL, 7 mmol) and benzotriazol-1-yloxytris(dimethylamino)phosphonium hexafluorphosphate (1.64 g, 3.6 mmol) in dimethylformamide according to the general procedure described in Example 1 for the preparation of N-(3-pyridylmethyl)-5-chloro-3-phenylthio-2-carboxamide.

Step B: 2-Benzoly-5-chloro-3-phenylthioindole

N-Methoxy-N-methyl-5-chloro-3-phenylthioindole-2-carboxamide (0.24 g, 0.69 mmol) was dissolved in dry tetrahydrofuran (5 mL) and cooled to −78° C. under nitrogen. A solution of phenylmagnesium chloride in tetrahydrofuran (0.81 mL, 2M) was added via syringe and the reaction warmed to 20° C. overnight. Water and ethyl acetate were added to the reaction and then separated. The organic phase was washed with water, 5% aqueous hydrochloric acid, saturated sodium bicarbonate, saturated brine, and dried over magnesium sulfate. Filtration and evaporation of solvent gave the crude product which was chromatographed on silica gel with 10% ether in hexane. The title compound was obtained as a solid, mp 154°–155° C. Anal. calc. for $C_{21}H_{14}ClNOS$: C, 69.32; H, 3.88; N, 3.85. Found: C, 68.61; H, 3.83; N, 3.83.

EXAMPLE 9

Preparation of 2-(2-Benzoxazol-2-ylethyl)-3-phenylthioindole

Step A: N-Methoxy-N-methyl-3-phenylthioindole-2-carboxamide

The title compound was prepared from 3-phenylthioindole-2-carboxylic acid (1.0 g, 3.7 mmol), N,O-dimethylhydroxylamine hydrochloride (0.54 g, 5.5 mmol), triethylamine (1.5 mL, 11 mmol) and benzotriazol-1-yloxytris(dimethylamino)phosphonium hexafluorphosphate (1.64 g, 3.7 mmol) according to the procedure described in Example 1 for N-(3-pyridylmethyl)-5-chloro-3-phenylthio-2-carboxamide.

Step B: 3-Phenylthioindole-2-carboxaldehyde

N-Methoxy-N-methyl-3-phenylthioindole-2-carboxamide (1.57 g, 5.26 mmol) was dissolved in tetrahydrofuran (150 mL) and cooled to 0° C. under nitrogen. A solution of lithium aluminum hydride in tetrahydrofuran (5.76 mL, 1M) was added slowly via syringe and the reaction stirred a total of 1.5 h. Ethyl acetate (30 mL) was added, followed by saturated sodium potassium tartrate solution. The layers were separated and the organic phase washed with saturated brine and dried over magnesium sulfate. Filtration and evaporation of solvent gave the title compound as a yellow solid.

Step C: trans-2-(2-Benzoxazol-2-ylethenyl)-3-phenylthioindole n-Butyllithium in hexane (3.47 mL, 2.5M) was added to a solution of [(benzoxal-2-yl)methyl]diethylphosphonate (2.34 g, 8.68 mmol) in tetrahydrofuran (50 mL) at −78° C. under nitrogen. The reaction was stirred for 20 min., and warmed to −20° C. A solution of 3-phenylthioindole-2-carboxaldehyde (1.10 g, 4.34 mmol) in tetrahydrofuran (30 mL) was added and the reaction stirred at 20° C. overnight. Ethyl acetate and water were added and the layers separated. The organic layer was washed with saturated brine and dried over magnesium sulfate. The crude product was triturated with 1:1 hexane ethyl acetate and collected by filtration. The title compound was obtained as a yellow solid, mp 260° C. Anal. Calc. for $C_{23}H_{16}N_2OS$: C, 72,32; H, 4.58; N, 7.33. Found: C, 72.41; H, 4.50; N, 7.44.

Step D: 2-(2-Benzoxazol-2-ylethyl)-3-phenylthioindole

A solution of trans-2-(2-benzoxazol-2-ylethenyl)-3-phenylthioindole (0.420 g, 1.14 mmol) in 1:1 methanol/tetrahydrofuran (250 mL) was stirred under 1 atmosphere of hydrogen in the presence of 10% palladium on charcoal (100 mg). Additional catalyst was added as needed to drive the reaction to completion. The catalyst was removed by filtration, and the filtrate concentrated in vacuo. The resulting solid was triturated with 10% ethyl acetate in hexane and collected by filtration to afford the title compound, mp 192°–193° C. Anal. calc. for $C_{23}H_{18}N_2OS$: C, 72.80; H, 5.04; N, 7.38. Found: C, 72.78; H, 4.95; N, 7.45.

EXAMPLE 10

Preparation of N-2-Furanylmethyl-5-chloro-3-phenylthioindole-2-carboxamide

The title compound was prepared according to the procedure described in example 1, step B, except substituting 2-aminomethylfuran for 3-aminomethylpyridine. The dimethylformamide was removed in vacuo, and the residue triturated with 1:1 ethyl acetate-hexane and filtered. Recrystallization from acetonitrile gave the title compound, mp 214° C. Anal. Calc. for $C_{20}H_{15}ClN_2O_2S$: C, 62.74; H, 3.95; N, 7.32. Found: C, 62.27; H, 3.88; N, 7.41. NMR (DMSO-$d_6$): δ12.55 (1H, s), 8.72 (1H, t, J=6 Hz), 7.55 (1H, m), 7.54 (1H, d, J=8 Hz), 7.45 (1H, d, J=2 Hz), 7.15 (1H, tt, J=7, 1 Hz), 7.08 (1H, s), 7.06 (1H, d, J=8 Hz), 6.35 (1H, m), 6.18 (1H, m), 4.56 (2H, d, J=6 Hz).

EXAMPLE 11

Preparation of N-3-Pyridyl-5-chloro-3-phenylthioindole-2-carboxamide

The title compound was prepared according to the procedure described in example 1, step B, except substituting 3-aminopyridine for 3-aminomethylpyridine. The dimethylformamide was removed in vacuo, and the residue triturated with 1:1 ethyl acetate-hexane and filtered. Chromatography on silica gel with 40% ethyl acetate in hexane gave the title compound, mp 255°–256° C. Anal. Calc. for $C_{20}H_{15}ClN_3OS$: C, 63.24; H, 3.98; N, 10.74. Found: C, 62.59; H, 3.86; N, 11.06. NMR (DMSO-$d_6$): δ12.72 (1H, s), 10.55 (1H, s), 8.85 (1H, d, J=3 Hz), 8.35 (1H, dd, J=5, 1 Hz), 8.14 (1H, dm, $J_d$=8 Hz), 7.60 (1H, d, J=9 Hz), 7.48 (1H, d, J=2 Hz), 7.40 (1H, dd, J=9, 2 Hz), 7.25 (2H, t, J=7 Hz), 7.16 (1H, m), 7.11 (2H, t, J=7 Hz).

EXAMPLE 12

Preparation of N-Ethyl-5-chloro-3-phenylthioindole-2-carboxamide

The title compound was prepared according to the procedure described in example 1, step B, except substituting ethylamine for 3-aminomethylpyridine. The dimethylformamide was removed in vacuo, and the residue triturated with 1:1 ethyl acetate-hexane and filtered. Recrystallization from 2% methanol in ethyl acetate gave the title compound, mp 210°–211° C. Anal. Calc. for $C_{17}H_{15}ClN_2OS \cdot 0.5 H_2O$: C, 60.08; H, 4.74; N, 8.24. Found: C, 60.00; H, 4.18; N, 8.52. NMR (DMSO-$d_6$): δ12.49 (1H, s), 8.31(1H, t, J=6 Hz), 7.54 (1H, d, J=9 Hz), 7.43 (1H, d, J=2 Hz), 7.27 (3H, m), 7.15 (1H, tt, J=7, 2 Hz), 7.07 (2H, m), 3.35(4H, m), 1.06 (3H, t, J=7 Hz).

EXAMPLE 13

Preparation of N-3-Methoxybenzyl-5-chloro-3-phenylthioindole-2-carboxamide

The title compound was prepared according to the procedure described in example 1, step B, except substituting 3-methoxybenzylamine for 3-aminomethylpyridine. The dimethylformamide was removed in vacuo, and the residue triturated with 1:1 ethyl acetate-hexane and filtered. Recrystallization from acetonitrile gave the title compound, mp 172° C. Anal. Calc. for $C_{23}H_{19}ClN_2O_2S \cdot 0.3 H_2O$: C, 64.48; H, 4.61; N, 6.54. Found: C, 64.41; H, 4.38; N, 6.75. NMR (DMSO-$d_6$): δ12.55 (1H, s), 8.80 (1H, m), 7.55 (1H, d, J=8 Hz), 7.44 (1H, s), 7.25 (3H, m), 7.15 (2H, m), 7.05 (2H, d, J=7 Hz), 6.80 (3H, m), 4.54 (2H, d, J=6 Hz).

EXAMPLE 14

Preparation of N-2-Methoxyethyl-5-chloro-3-phenylthioindole-2-carboxamide

The title compound was prepared according to the procedure described in example 1, step B, except substituting 2-methoxyethylamine for 3-aminomethylpyridine. The dimethylformamide was removed in vacuo, and the residue triturated with 1:1 ethyl acetate-hexane and filtered to give the title compound, mp 216°–217° C. Anal. Calc. for $C_{18}H_{17}ClN_2O_2S \cdot 0.25 H_2O$: C, 59.17; H, 4.83; N, 7.67. Found: C, 59.11; H, 4.75; N, 7.82. NMR (DMSO-$d_6$): δ12.54 (1H, s), 8.44 (1H, t, J=6 Hz), 7.54 (1H, d, J=9 Hz), 7.48 (1H, d, J=2 Hz), 7.28 (3H, m), 7.17 (1H, t, J=7 Hz), 7.10 (2H, m), 3.49 (2H, q, J=6 Hz), 3.37 (2H, t, J=6 Hz), 3.16 (3H, s).

EXAMPLE 15

Preparation of N-4-Pyridylmethyl-5-chloro-3-phenylthioindole-2-carboxamide

The title compound was prepared according to the procedure described in example 1, step B, except substituting 4-aminomethylpyridine for 3-aminomethylpyridine. The dimethylformamide was removed in vacuo, and the residue triturated with 1:1 ethyl acetate-hexane and filtered. Recrystallization from acetonitrile gave the title compound, mp 228°–229° C. Anal. Calc. for $C_{21}H_{16}ClN_3OS$: 0.2 $H_2O$: C, 63.45; H, 4.16; N, 10.57. Found: C, 63.33; H, 4.02; N, 10.50. NMR (DMSO-$d_6$): δ12.56 (1H, s), 8.92 (1H, t, J=6 Hz), 8.38 (1H, d, J=4 Hz), 7.55 (1H, d, J=8 Hz), 7.47 (1H, s), 7.31 (1H, dd, J=8, 2 Hz), 7.25 (1H, d, J=7 Hz), 7.17 (2H, m), 7.05 (1H, d, J=7 Hz), 4.58 (2H, d, J=6 Hz).

EXAMPLE 16

Preparation of N-2-Hydroxyethyl-5-chloro-3-phenylthiodindole-2-carboxamide

The title compound was prepared according to the procedure described in example 1, step B, except substituting 2-hydroxyethylamine for 3-aminomethylpyridine. The dimethylformamide was removed in vacuo, and the residue triturated with 1:1 ethyl acetate-hexane and filtered. Chromatography on silica gel with 2% methanol in chloroform gave the title compound, mp 222°–223° C. Anal. Calc. for $C_{17}H_{15}ClN_2O_2S$: 0.3 $H_2$: C, 57.96; H, 4.46; N, 7.95. Found: C, 57.99; H, 4.26; N, 7.90. NMR (DMSO-$d_6$): δ12.50 (1H, s), 8.46 (1H, m), 7.55 (1H, d, J=9 Hz), 7.45 (1H, d, J=1 Hz), 7.28 (3H, m), 7.17 (1H, t, J=6 Hz), 7.13 (2H, m), 4.85 (1H, t), 3.49 (1H, m), 3.43 (1H, m).

EXAMPLE 17

Preparation of 5-Chloro-3-phenylthioindole-2-carboxamide

The title compound was prepared according to the procedure described in example 1, step B, except substituting an excess of ammonia gas for 3-aminomethylpyridine and triethylamine. The dimethylformamide and excess ammonia were removed in vacuo and the residue partitioned between ethyl acetate and 10% hydrochloric acid. The organic phase was washed with water, 5% sodium hydroxide and saturated brine, and then dried over magnesium sulfate. Filtration and evaporation gave a crude product which was chromatographed on silica gel with 30% ethyl acetate in hexane. The title compound was obtained as a white solid mp 213°–215° C. Anal. Calc. for $C_{15}H_{11}ClN_2OS \cdot \frac{1}{3}H_2O$: C, 58.35; H, 3.81; N, 9.07. Found: C, 58.33; H, 3.64; N, 9.11. NMR (DMSO-$d_6$): δ12.52 (1H, bs), 8.06 (1H, s), 7.76 (1H, s), 7.55 (1H, d, J=9 Hz), 7.44 (1H, s), 7.28 (3H, m), 7.15 (1H, t, J=6 Hz), 7.06 (2H, d, J=8 Hz).

EXAMPLE 18

Preparation of 5-Chloro-3-phenylthioindole-2-thiocarboxamide

A solution of 5-chloro-3-phenylthioindole-2-carboxamide (3.8 g, 12.5 mmol) and [2,4-bis(4-methoxyphenyl)-1,3-dithia-2,4-diphosphetane-2,4-disulfide (Lawesson's reagent) (5.0 g, 12.5 mmol) in dry THF (110 mL) was refluxed under nitrogen for 16 h. The solvent was removed in vacuo and the residue chromatographed on silica gel with 10% ethyl acetate in hexane. The chromatographed product was triturated with hexane and the yellowish solid collected and dried to give the title compound, mp 217° C. (decomposed). Anal. Calc. for $C_{15}H_{11}ClN_2S$: C, 56.50; H, 3.48; N, 8.79. Found: C, 56.75; H, 3.64; N, 8.59. NMR (DMSO-$d_6$): δ12.22 (1H, s), 10.31 (1H, s), 9.48 (1H, s), 7.50 (1H, d, J=8 Hz), 7.39 (1H, s), 7.25 (3H, m), 7.13 (1H, t, J=7 Hz), 7.01 (2H, d, J=7 Hz).

EXAMPLE 19

Preparation of N-2-furanylmethyl-5-chloro-3-phenylthioindole-2-thiocarboxasmide

The title compound was prepared according to the procedure described for 5-chloro-3-phenylthioindole-2-thiocarboxamide except substituting N-2-furanylmethyl-5-chloro-3-phenylthioindole-2-carboxamide for 5-chloro-3-phenylthioindole-2-carboxamide. The crude product was chromatographed on silica gel with 3% ethyl acetate in hexane. The title compound was obtained as a bright yellow solid, mp 143°–144° C. Anal. Calc. for $C_{20}H_{15}ClN_2OS_2 \cdot H_2O$: C, 57.61; H, 3.62; N, 6.72. Found: C, 57.56; H, 3.58; N, 6.52. NMR (DMSO-$d_6$): δ12.27 (1H, s), 10.73 (1H, s), 7.55 (2H, m), 7.39 (1H, s), 7.21 (4H, m), 6.98 (2H, d, J=7 Hz), 6.36 (2H, 4.96 (2H, s).

EXAMPLE 20

Preparation of N-[1-(2(R)-hydroxypropyl)]-5-chloro-3-phenylthioindole-2-carboxamide The title compound was prepared according to the procedure described in example 1, step B, except substituting 2(R)-hydroxy-1-propylamine for 3-aminomethylpyridine. The dimethylformamide was removed in vacuo and the residue triturated first with 20% ethyl acetate in hexane then by acetonitrile. The title compound was obtained as an off-white solid, mp 202°–203° C. Anal. Calc. for $C_{18}H_{17}ClN_2O_2S \cdot 0.3 H_2O$: C, 59.01; H, 4.67; N, 7.65. Found: C, 58.91; H, 4.59; N, 7.50. NMR (DMSO-$d_6$): δ12.52 (1H, s), 8.45 (1H, t, J=5 Hz), 7.55 (1H, d, J=8 Hz), 7.46 (1H, s), 7.25 (3H, m), 7.15 (3H, m), 4.89 (1H, d, J=5 Hz), 3.74 (1H, m), 3.38 (1H, m), 3.23 (1H, m), 1.00 (3H, d, J=6 Hz).

EXAMPLE 21

Preparation of N-(2-pyridyl)methyl-5-chloro-3-phenylthioindole-2-carboxamide

The title compound was prepared according to the procedure described in example 1, step B, except substituting 2-pyridylmethylamine for 3-aminomethylpyridine. The dimethylformamide was removed in vacuo and the residue triturated first with 30% ethyl acetate in hexane, then with acetonitrile. The title compound was obtained as a white solid, mp 209°–210° C. Anal. Calc. for $C_{21}H_{16}ClN_3OS$: C, 64.03; H, 4.10; N, 10.67. Found: C, 63.51; H, 3.97; N, 10.41. NMR (DMSO-$d_6$): δ12.58 (1H, s), 9.15 (1H, t, J=5 Hz), 8.46 (1H, d, J=5 Hz), 7.66 (1H, t, J=8 Hz), 7.57 (1H, d, J=8 Hz), 7.50 (1H, s), 7.25 (5H, m), 7.12 (3H, m), 4.68 (2H, d, J=5 Hz).

EXAMPLE 22

Preparation of N-(3-methoxy-4-pyridyl)methyl-5-chloro-3-phenylthioindol-2-carboxamide Step 1: Preparation of 4-cyano-2-methoxypyridine A solution of 2-chloro-4-cyanopyridine (1.25 g, 9.1 mmol), prepared as described by D. Libermann, N. Rist, F. Grumbach, S. Cals, M. Moyeux and A. Rouaix, *Bull. Soc. Chim. France*, 694 (1958), in methanol was treated with sodium methoxide (0.58 g, 10.9 mmol) and refluxed for 30 minutes. The reaction mixture was cooled, filtered and the filtrate concentrated in vacuo to obtain the crude product as an off-white solid. The crude product was chromatographed on silica gel with 20% ethyl acetate in hexane. The title compound was obtained as a white powder.

Step 2: Preparation of 4-aminomethyl-2-methoxypyridine

A solution of 4-cyano-2-methoxypyridine (0.55 g, 4.1 mmol) in ethanol was hydrogenated at 60 psi $H_2$ in the presence of 10% Pd/C (100 mg). After 3.5 h the catalyst was removed by filtration through Super-Gel and the liltrate evaporated to give the title compound as a foam.

Step 3: Preparation of N-(3-methoxy-4-pyridylmethyl)-5-chloro-3-phenylthioindole-2-carboxamide The title compound was prepared according to the procedure described in example 1, step B, except substituting 4-aminomethyl-2-methoxypyridine for 3-aminomethylpyridine. The dimethylformamide was removed in vacuo and the crude product purified by chromatography on silica gel with 20–40% ethyl acetate in hexane. The title compound was obtained as a white solid, mp 227°–228° C. Anal. Calc. for $C_{22}H_{18}ClN_3O_2S$: C, 62.33; H, 4.28; N, 9.91. Found: C, 62.63; H, 4.21; N, 9.92. NMR (DMSO-$d_6$): δ12.58 (1H, s), 8.93 (1H), 8.37 (2H, d), 7.56 (1H, d), 7.47 (1H, s), 7.27 (3H, m), 7.18 (2H, m), 7.05 (2H, d), 4.59 (2H, d), 3.30 (3H, s).

EXAMPLE 23

Preparation of N-(3-hydroxymethyl)benzyl-5-chloro-3-phenylthioindole-2carboxamide The title compound was prepared according to the procedure described in example 1, step B, except substituting 3-hydroxymethylbenzylamine for 3-aminomethylpyridine. The dimethylformamide was removed in vacuo and the crude product recrystallized from acetonitrile. The title compound was obtained as a white solid, mp 229°–230° C. Anal. Calc. for $C_{22}H_{17}ClN_2O_2S$: C, 64.61; H, 4.19; N, 6.85. Found: C, 64.20; H, 4.09; N, 6.85. NMR (DMSO-$d_6$): δ12.69 (1H, s), 10.33 (1H, s), 7.60 (3H, m), 7.49 (1H, s), 7.30 (4H, m), 7.15 (4H, m), 5.22 (1H, t, J=7 Hz), 4.50 (2H, d, J=7 Hz).

EXAMPLE 24

Preparation of N-(3-hydroxybenzyl)-5-chloro-3-phenylthioindole-2-carboxamide

The title compound was prepared according to the procedure described in example 1, step B, except substituting 3-hydroxybenzylamine for 3-aminomethylpyridine. The dimethylformamide was removed in vacuo and the crude product was chromatographed on silica gel with 10% methanol in chloroform. The title compound was obtained as a white solid, mp 214°. 216° C. Anal. Calc. for $C_{22}H_{17}ClN_2O_2S\cdot0.3\ H_2O$; C, 63.77; H, 4.04; N, 6.76. Found: C, 63.92; H, 3.88; N, 6.49. NMR (DMSO-$d_6$): δ12.55 (1H, s), 9.34 (1H, s), 8.75 (1H, t, J=5 Hz), 7.53 (1H, d, J=8 Hz), 7.45 (1H, s), 7.1–7.65 (4H, m), 7.06 (2H, d, J=7 Hz), 7.01 (1H, t, J=8 Hz), 6.70 (1H, s), 6.62 (2H, m), 4.48 (2H, d, J=5 Hz).

EXAMPLE 25

Preparation of 5-Chloro-3-phenylsulfonylindole-2-carboxamide (Compound 18)

5-Chloro-3-phenylthioindole-2-carboxamide (0.177 g, 0.584 mmol) was dissolved in 25 mL chloroform and cooled to 0° C. 50% By weight meta-chloroperoxybenzoic acid (503 mg, 1.46 mmol) was added and the reaction stirred at 20° C. for 6 hours. A 10% aqueous solution of sodium thiosulfate was added and the reaction vigorously stirred for 10 minutes. The layers were separated and the organic phase washed with saturated sodium chloride then dried over magnesium sulfate. The crude product was chromatographed over silica gel eluting with 40% ethyl acetate in hexane. The title compound was obtained as a white powder, mp 255°–257° C. NMR (300 MHz, DMSO-d6): δ13.05 (1H,s), 8.48(1H,s), 8.25(1H,s), 8.03(2H,d,J=8 Hz), 7.95(1H, s), 7.60(4H,m), 7.34(1H,d,J=8 Hz). Anal. Calc. for $C_{15}H_{11}ClN_2O_3S$: C, 53.82; H, 3.31; N, 8.37. Found: C, 53.74; H, 3.29; N, 8.34

EXAMPLE 26

Preparation of 5-Chloro-3-phenylsulfinylindole-2-carboxamide (Compound 17)

A solution of magnesium monoperoxyphthalic acid (85% peracid) (11.8 mg, 0.024 mmol) in methanol (2 mL) was added dropwise to a solution of 5-chloro-3-phenylthioindole-2-carboxamide (14.5 mg, 0.048 mmol) in methanol (2 mL) at 0° C. The reaction was stirred at 20° C. for 4 hours. A solution of 10% aqueous sodium thiosulfate was added and the reaction stirred vigorously for 10 minutes. Methanol was removed in vacuo and the residue partitioned between ethyl acetate and water. The ethyl acetate extract was washed with brine and dried over magnesium sulfate. The crude product was purified by column chromatography on silica gel with 30–40% ethyl acetate in hexane. The title compound was obtained as a white solid. NMR, (DMSO-$d_6$, 300 MHz) δ12.53(1H, s), 8.35(1H,br s), 8.08(1H,br s), 7.83(1H,d,J=2 Hz), 7.71(2H,d,J=8 Hz), 7.52(4H,m), 7.30(1H,dd,J=9,2 Hz).

EXAMPLE 27

Preparation of N-(2,6-difluorobenzyl)-5-chloro-3-phenylsulfonylindole-2-carboxamide Step A: 5-chloro-3-phenylsulfonylindole-2-carboxylic acid To a suspension of 5-chloro-3-phenylthio-indole-2-carboxylic acid (4.84 g, 0.016 mol) in chloroform (1200 mL) was added 55% m-chloroperoxybenzoic acid (12.5 g, 0.04 mol). The mixture was allowed to stir at room temperature for 40 hours. Filtration afforded the title compound as a colorless solid, mp 277°–280° C (dec). On partial evaporation a second crop of product was obtained.

Step B: Product of reaction of 5-chloro-3-phenylsulfonylindole-2-carboxylic acid with oxalyl chloride To a suspension of 5-chloro-3-phenylsulfonylindole-2-carboxylic acid (5.04 g, 0.015 mol) in chloroform (200 mL) was added oxalyl chloride (3.81 g, 0.03 mol). After addition of a catalytic amount of dimethylformamide (0.1 mL) the mixture was heated at a bath temperature of 60° C. for 50 minutes. After cooling, the solid product, mp >300° C., was utilized directly without further purification. While based on mass spectral and NMR data, this product appears to be a symmetrical dimer, it behaves as a typical acid chloride in reactions with primary amines.

Step C: N-(2,6-difluorobenzyl)-5-chloro-3-phenylsulfonylindole-2-carboxamide 2,6-Difluorobenzylamine (0.430 g, 3.0 mmol) was added dropwise to the solution of the "acid chloride equivalent" from Step B (0.354 g, 1.0 mmol) in tetrahydrofuran solution (10 mL) cooled in an ice-acetone bath. The reaction mixture was allowed to warm to room temperature and left overnight. For work-up, ethyl acetate and water were added. The ethyl acetate phase was washed well with dilute hydrochloride acid, saturated aqueous sodium bicarbonate, and brine. After drying over magnesium sulfate and evaporation of the solvent, the residue was slurried with ethyl acetate and filtered to give the title compound, mp 274°–280° C. Anal. calc'd for $C_{22}H_{15}ClF_2N_2O_3S\cdot0.5H_2O$: C, 56.24; H, 3.43; N, 5.96 Found: C, 56.12; H, 3.31; N, 5.97. NMR (DMSO-$d_6$) $\delta$13.06 (1H, s), 9.41 (1H, t, J=5.5 Hz), 7.95 (3H, m), 7.41–7.67 (m, 5H), 7.34 (1H, dd, J=9, 2 Hz), 7.18 (2H, t, J=8 Hz), 4.64 (2H, d, J=5.5 Hz).

EXAMPLE 28

Preparation of N-(4-pyridylmethyl)-5-chloro-3-phenylsulfinylindole-2-carboxamide (29)

Step A: Preparation of 5-chloro-3-phenylsulfinylindole-2-carboxylic acid

To a suspension of 5-chloro-3-phenylthioindole-2-carboxylic acid (2.14 g, 0.007 mol) in chloroform (600 mL) was added 55% m-chloroperoxybenzoic acid (2.32 g, 0.0074 mol). The mixture cleared briefly and then solids appeared. After stirring overnight at room temperature, the title compound was obtained in pure form on filtration, mp 183°–185° C.

Step B: N-(4-pyridylmethyl)-5-chloro-3-phenylsulfinylindole-2-carboxamide

To a mixture of 5-chloro-3-phenylsulfinylindole-2-carboxylic acid (0.096 g, 0.3 mmol), triethylamine (0.061 g, 0.6 mmol), 4-aminomethylpyridine (0.043 g, 0.4 mmol) in dry dimethylformamide was added benzotriazol-1-yloxytris-(dimethylamino)phosphonium hexafluorophosphate (BOP reagent) (0.155 g, 0.35 mmol). The mixture was stirred at room temperature under nitrogen for three days. Following evaporation, the residue was partitioned between ethyl acetate and water. The ethyl acetate phase was separated and washed with dilute hydrochloric acid. The acidic extract was neutralized with aqueous sodium bicarbonate and the product extracted into ethyl acetate. The ethyl acetate extract was washed well with aqueous sodium bicarbonate, then brine, and dried over magnesium sulfate. Evaporation afforded a solid residue which was recrystallized from ethyl acetate to give the title compound, mp 233°–235° C. Anal. Calcd for $C_{21}H_{16}ClN_3O_2S$: C, 61.54; H, 3.93; N, 10.25. Found: C, 61.39; H, 3.95; N, 10.36. NMR (DMSO-$d_6$) $\delta$9.62 (1H, t, J=6 Hz), 8.53 (2H, d, J=6 Hz), 7.80 (1H, d, J=2 Hz), 7.67 (2H, m), 7.64 (2H, d, J=9 Hz), 7.44–7.54 (3H, m), 7.33 (3H, m), 4.60 (2H, dq, J=9, 6 Hz).

EXAMPLE 29

Preparation of N-[(S)-1-phenyl-2-hydroxyethyl]-5-chloro-3-phenylsulfonylindole-2-carboxamide (32)

To a solution of the acid chloride dimer product from Example 27, Step B, (0.354 g, 1.0 mmol) in tetrahydrofuran (10 mL), cooled in an ice-acetone bath, was added a solution of (S)-(+)-2-phenylglycinol (0.343 g, 2.5 mmol). The mixture, after warming gradually to room temperature, was allowed to sit overnight. Ethyl acetate and water were added. The ethyl acetate phase was washed successively with dilute hydrochloric acid, water, saturated sodium bicarbonate and brine. After drying over magnesium sulfate and evaporation, the product was chromatographed on a 20 mm column containing 6 inches of 230–400 mesh silica gel. Elution with 40% ethyl acetate-methylene chloride gave pure title compound which, after evaporation, was crystallized from ethyl acetate-hexane to give the title compound, mp 155°–160° C. Anal Calc. for $C_{23}H_{19}ClN_2O_4S$: C, 60.72; H, 4.21; N, 6.16. Found: C, 60.33; H, 4.13; N, 6.16. NMR (DMSO-$d_6$): $\delta$13.05 (1H, s), 9.52 (1H, d, J=7.5 Hz), 7.95–8.48 (3H, m), 7.26–7.68 (10H, m), 5.13 (1H, q, J=7.5 Hz), 5.07 (1H, t=6 Hz), 3.75 (2H, 6 Hz).

EXAMPLE 30

N-(3-methoxybenzyl)-5-chloro-3-(2-thiazolyl)-sulfonylinde-2-carboxamide (31)

Step A: Preparation of 5-Chloro-3-(2-thiazolyl)thioindole-2-carboxylic Acid.

Using the procedure of Example 1, Step A, but substituting di-(2-thiazolyl)disulfide for phenyldisulfide, there was obtained the title compound, mp 242°20 –244°20 C.

Step B: Preparation of 5-Chloro-3-(2-thiazolyl)sulfonylindole-2-carboxylic Acid

Using the procedure of Example 27, Step A, but substituting 5-chloro-3-(2-thiazolyl)thioindole-2-carboxylic acid for 5-chloro-3-phenylthioindole-2-carboxylic acid, there was obtained the title compound, mp 260°–261° C.

Step C: Product of Reaction of 5-Chloro-3-(2-thiazolyl)sulfonylindole-2-carboxylic Acid with Oxalyl Chloride Using the procedure of Example 27, Step B, but substituting 5-chloro-3-(2-thiazolyl)sulfonylindole-2-carboxylic acid for 5-chloro-3-phenylsulfonylindole-2-carboxylic acid, there was obtained a solid product, mp>290° C., which was utilized directly in the next step.

Step D: N-(3-methoxybenzyl)-5-chloro-3-(2-thiazolylsulfonyl)indole-2-carboxamide To a solution of the 'acid chloride' product from Step C (0.181 g, 0.5 mmol) in tetrahydrofuran (5 mL), cooled in an ice-acetone bath, was added 3-methoxybenzylamine (0.205 g, 1.5 mmol). The mixture was allowed to warm to room temperature and then was left overnight with stirring. Ethyl acetate and water were added. The ethyl acetate layer, after separation, was washed with dilute hydrochloric acid, saturated sodium bicarbonate, and brine. After drying (magnesium sulfate) and evaporation, the solid residue was allowed to stand in a small volume of ethyl acetate. Filtration gave the title product, mp 205°–209° C. Anal. calcd for $C_{20}H_{16}ClN_3O_4S_2$: C, 52.00, H, 3.49, N, 9.10. Found: C, 51.88 H, 3.42, N, 9.07 (DMSO-$d_6$) $\delta$9.43 (1H, t, J=6 Hz), 8.18 (1H, d, J=3 Hz), 8.02 (1H, d, J=3 Hz), 8.00 (1H, d, J=2 Hz), 7.58 (1H, d, J=8.5 Hz), 7.40 (1H, dd, J=8.5, 2 Hz), 7.28 (1H, t, J=8 Hz), 6.98–7.05 (2H, m), 6.85 (1H, dd, J=8, 2.5 Hz), 4.54 (2H, d, J=3.76 Hz).

EXAMPLE 31

5-Chloro-3-(2-thiazolyl)sulfonylindole-2-carboxamide

A solution of the 'acid chloride' product of Example 30, Step C, (0.50 g, 1.4 mmol) in tetrahydrofuran (25 mL) was added slowly to a solution of tetrahydrofuran saturated with ammonia at −10° C. The reaction mixture was allowed to warm gradually to room temperature and then was stirred overnight. After evaporation of the solvent, the residue was partitioned between ethyl acetate and water. The ethyl acetate extract was washed with saturated sodium bicarbonate and brine, and dried with magnesium sulfate. After evaporation of solvent, the residue was slurried in ethyl acetate and filtered to give the title compound, mp 292°–294° C. (dec). Anal. calcd for $C_{12}H_8ClN_3O_3S_2$: C, 42.17; H, 2.36; N, 12.29. Found: 42.23; H, 2.35; N, 11.85. NMR (DMSO-$d_6$) δ8.39 (1H, br s), 8.34 (1H, br s), 8.24 (1H, d, J=3 Hz), 8.07 (1H, d, J=3 Hz), 8.00 (1H, dd, J=2, 0.6 Hz), 7.57 (1H, dd, J=9, 0.6 Hz), 7.40 (1H, dd, J=9, 2 Hz).

EXAMPLE 32

5-Chloro-3-phenylsulfonylindole-2-thiocarboxamide

Reaction of 5-chloro-3-phenylsulfonylindole-2-carboxamide with 2,4-bis(4-methoxyphenyl)-1,3-dithia-2,4-diphosphetane (Lawesson's reagent) according to the procedure of Example 18 gave the title compound. Chromatographic purification on silica gel was carried out using 30% ethyl acetate-methylene chloride, followed by 50% ethyl acetate-methylene chloride. The pure product had mp 207°–210° C. Anal. calcd for $C_{15}H_{11}ClN_2O_2S_2$: C, 51.35; H, 3.16; N, 7.98. Found: C, 50.84; H, 3.08; N, 8.04. NMR (DMSO-$d_6$) δ12.90 (1H, s), 10.71 (1H, s), 10.70 (1H, s), 8.0–8.6 (2H, m), 7.84 (1H, d, J=2 Hz), 7.54–7.66 (3H, m), 7.46 (1H, d, J=8.5 Hz), 7.30 (1H, dd, J=8.5, 2 Hz).

EXAMPLE 33

Preparation of 3-phenylsulfonyl-5-chloroindole-2-carboxamide

Step A: N-(phenylthio)succinimide

To a partial solution of N-chlorosuccinimide (3.34 g, 25 mmol) in dry methylene chloride (30 mL), cooled in an ice bath and under an inert atmosphere, was added thiophenol (2.05 mL, 20 mmol) via syringe. After stirring for 1 hour, additional N-chlorosuccinimide (0.40 g, 3 mmol) was added. After 2.5 hours total, triethylamine (3.9 mL, 28 mmol) was added dropwise. Within 15 minutes the reaction mixture was diluted with methylene chloride, the solvent washed with dilute aq. HCl and the solvent then dried ($Na_2SO_4$), filtered through a pad of charcoal and evaporated. The residue was triturated with diethyl ether and the product collected by filtration to yield the title compound mp 115°–116° C. [lit. mp 115°–116° C., *J. Org. Chem.*, 34, 51 (1969)]. This material was used as is.

Step B: Ethyl 3-phenylthio-5-chloroindole-2-carboxylate

To a partial suspension of ethyl 5-chloroindole-2-carboxylate (698 mg, 3.1 mmol) and N-(phenylthio)succinimide (683 mg, 3.3 mmol) in anhydrous methylene chloride (20 mL) at ambient temperature under an inert gas atmosphere was added boron trifluoride etherate (0.12 mL, 1.0 mmol). The reaction was monitored by tlc (thin layer chromatography) until complete. After 2 hours, the reaction was diluted with chloroform and neutralized with aq. $NaHCO_3$. The organic layer was dried ($Na_2SO_4$), filtered through a pad of charcoal, and the solvents evaporated. The residue was triturated with hexanes as the product crystallized out to yield the title product, mp 160°–162° C. [see Table II, mp 163°–164° C.]. This material was used as is.

Step C: Ethyl 3-phenylsulfonyl-5-chloroindole-2-carboxylate

Ethyl 3-phenylthio-5-chloroindole-2-carboxylate (642 mg, 1.94 mmol) was dissolved in chloroform (35 mL) and a dried ($Na_2SO_4$) solution of m-chloroperoxybenzoic acid (55% pure, 1.30 g, 4.1 mmol) in chloroform (20 mL) was added dropwise. The progress of the oxidation was monitored by tlc until complete. After 5 hours, the reaction was diluted with chloroform and some methanol and the solution washed with aq. $NaHCO_3$ and aq. $Na_2CO_3$. The dried ($Na_2SO_4$) organic layer was filtered through a pad of charcoal and the solvents removed under reduced pressure. The residue was triturated with diethyl ether to yield the product. Crystallization from methylene chloride and diethyl ether gave analytically pure material, mp 201°–202° C.

$^1$H NMR (CDCl$_3$) δ9.63 (br s, 1H), 8.58 (t, 1H, J=0.7 Hz), 8.07 (d, 2H, J=7 Hz), 7.46–7.56 (m, 3H), 7.40 (m, 2H), 4.39 (ABq, 2H, J=7 Hz), 1.35 (t, 3H, J=7 Hz).

Anal. calcd for $C_{17}H_{14}ClNO_4S$: C, 56.12; H, 3.88; N, 3.85. Found: C, 55.91; H, 3.95; N, 3.91.

Step D: 3-Phenylsulfonyl-5-chloroindole-2-carboxamide (Compound 18)

A suspension of ethyl 3-phenylsulfonyl-5-chloroindole-2-carboxylate (596 mg, 1.64 mmol) in aqueous conc. ammonium hydroxide (10 mL) containing ammonium chloride (28 mg) was heated at 100° C. for 3 hours in a sealed screw-top tube. The sealed tube was cooled in an ice bath as product crystallized out. The product was collected by filtration, rinsed with ice water, and dried to give the product, mp 253°–254° C.

EXAMPLE 34

Preparation of N-[(imidazol-2-yl)methyl]-3-phenylsulfonyl-5-chloroindole-2-carboxamide A suspension of 2-aminomethylimidazole dihydrochloride (256 mg, 1.5 mmol) [prepared as described in *J. Org. Chem.*, 43, 1603 (1978)] in dry tetrahydrofuran (6 mL) containing triethylamine (0.42 mL, 3.0 mmol) was stirred at room temperature under an inert atmosphere for one hour. The dimeric acid chloride (179 mg, 0.25 mmol) [see Example 27, Step B] was added, followed by additional triethylamine (0.07 mL, 0.5 mmol) and the mixture was stirred for 12–20 hours. The mixture was diluted with water and the product extracted into ethyl acetate. This organic layer was dried ($Na_2SO_4$), filtered, and the solvents evaporated. The residue was triturated with ethyl acetate to give the product. Recrystallization from hot ethyl acetate gave analytically pure product, mp 276°–278° C.

$^1$H NMR (DMSO-$d_6$) δ9.50 (br t, 1H, J=5.4 Hz), 8.07 (s, 1H), 8.05 (s, 1H), 8.00 (d, 1H, J=1.2 Hz), 7.52–7.67 (m, 4H), 7.37 (dd, 1H, J=1.5, 9 Hz), 7.03 (br s, 2H), 4.61 (d, 2H, J=5.4 Hz).

Anal. calcd for $C_{19}H_{15}ClN_4O_3S$: C, 55.00; H, 3.64; N, 13.50 Found: C, 54.67; H, 3.36; N, 13.37

EXAMPLE 35

Preparation of N-[(1-methylimidazol-2-yl)methyl]-3-phenylsulfonyl-5-chloroindole-2-carboxamide (19)

Step A: 2-Aminomethyl-1-methylimidazole

To a suspension of lithium aluminum hydride (114 mg, 3.0 mmol) in dry tetrahydrofuran (15 mL) at room temperature in an inert atmosphere was added solid 1-methylimidazole-2-carboxamide (185 mg, 1.5 mmol) [prepared according to *J. Org. Chem.*, 52, 4379 (1987)] in portions.

After stirring the reaction mixture for 0.5 hour, the temperature was raised to 50° C. for 3.5 hours. After cooling this reaction, satd. aq. Na$_2$SO$_4$ (2 mL) was added to quench reaction and then powdered anhyd. Na$_2$SO$_4$. Filtration of this mixture to remove salts gave a dry solution of 2-aminomethyl-1-methylimidazole in tetrahydrofuran (~25 mL) which was used as is.

Step B: N-[(1-methylimidazol-2-yl)methyl]-3-phenylsulfonyl-5-chloroindole-2-carboxamide A solution of the dimeric indole acid chloride (see Example 27, Step B) (358 mg, 0.5 mmol) in dry tetrahydrofuran (7 mL) was added dropwise to the above solution of 2-aminomethyl-1-methylimidazole in tetrahydrofuran, which was cooled in an ice bath. After 15 min. triethylamine (0.2 mL, 1.4 mmol) was added and the reaction mixture slowly warmed to room temperature over 12–20 hours. The reaction was diluted with water and the product extracted into 10% methanol/ethyl acetate. The extract was dried (Na$_2$SO$_4$), filtered through charcoal, and the solvents evaporated. The residue was triturated with ethyl acetate and the product collected by filtration. Recrystallization from hot methanol/ethyl acetate gave analytically pure material, mp 273°–275° C.

$^1$H NMR (DMSO-d$_6$) δ9.48 (br t, 1H, J=5 Hz), 8.05 (d, 2H, J=7 Hz), 7.98 (d, 1H, J=2 hz), 7.52–7.67 (m, 4H), 7.35 (dd, 1H, J=2, 9 Hz), 7.18 (d, 1H, J=1 Hz), 6.88 (d, 1H, J=1 Hz), 4.66 (d, 2H, J=5 Hz), 3.71 (s, 3H).

Anal. calcd for C$_{20}$H$_{17}$ClN$_4$O$_3$S: C, 56.00; H, 4.00; N, 13.06 Found: C, 55.77; H, 3.97; N, 13.41

The hydrochloride salt was obtained by addition of one equivalent of ethanolic HCl to the free base, mp 284°–285° C. with decomposition.

Anal. calcd for C$_{20}$H$_{17}$ClN$_4$O$_3$S.HCl: C, 51.62; H, 3.90: N, 12.04 Found: C, 51.21; H, 3.92; N, 11.55

EXAMPLE 36

Alternate Preparation of N-[(1-methylimidazol-2-yl)methyl] 3-phenylsulfonyl-5-chloroindole-2-carboxamide To a partial suspension of N-[(imidazol-2-yl)methyl] 3-phenylsulfonyl-5-chloroindole-2-carboxamide (Example 35) (42 mg, 0.1 mmol) in 1:1 methanol/tetrahydrofuran (4 mL) was added iodomethane (0.05 mL, 0.8 mmol). The reaction was stirred for three days at room temperature. The solvents were removed under reduced pressure, aq. NaHCO$_3$ added and the product extracted into ethyl acetate/methanol. The organic layer was dried (Na$_2$SO$_4$), filtered, and the solvents evaporated. The residue was purified by chromatography and the product eluted with 3% methanol/chloroform. Appropriate fractions were combined, the solvents evaporated, and the residue triturated with methylene chloride to give pure product.

EXAMPLE 37

Preparation of N-[2-(imidazol-4-yl)ethyl]-3-phenylsulfonyl-5-chloroindole-2-carboxamide (24)

Carbonyldiimidazole (180 mg, 1.11 mmol) was added to a solution of 5-chloro-3-phenylsulfonylindole-2-carboxylic acid (Example 27, Step A) (336 mg, 0.5 mmol) cooled in an ice bath under an inert atmosphere. After 0.5 hours, histamine (125 mg, 1.12 mmol) was added to the yellow solution. After 5 hours the reaction was diluted with water and the product extracted into ethyl acetate. This organic layer was washed with dilute aq. NaHCO$_3$, dried (Na$_2$SO$_4$), filtered through charcoal and the solvents evaporated. Trituration of this residue with methylene chloride gave the crude product. Crystallization from hot ethyl acetate gave analytically pure product, mp 220°–221.5° C.

$^1$H NMR (DMSO-d$_6$) δ9.11 (br t, 1H, J=5.4 Hz), 8.00 (s, 1H), 7.98 (s, 1H), 7.95 (d, 1H, J=2.1 Hz), 7.52–7.67 (m, 5H), 7.35 (dd, 1H, J=2.1, 8.7 Hz), 6.94 (s, 1H), 3.60 (q, 2H, J=7.2 Hz), 2.83 (t, 2H, J=7.2 Hz).

Anal calcd for C$_{20}$H$_{17}$ClN$_4$O$_3$S: C, 56.00; H, 4.00; N, 13.05 Found: C, 55.74; H, 4.04; N, 13.35

EXAMPLE 38

Preparation of N-(3-methoxybenzyl)-3-phenylsulfonyl-5-chloroindole-2-carboxamide A solution of dimeric acid chloride (Example 27, Step B) (1.77 g, 2.5 mmol) in dry tetrahydrofuran (25 mL) was added dropwise to a solution of 3-methoxybenzylamine (1.3 mL, 10 mmol) in dry tetrahydrofuran (20 mL) cooled with an ice acetone bath. The reaction was stirred for 12–20 hours and then diluted with 10% methanol/ethyl acetate. This organic layer was washed with dilute HCl, dried (Na$_2$SO$_4$), filtered, and the solvents evaporated. The residue was triturated with diethyl ether to give flocculent white product. Recrystallization from hot methanol/ethyl acetate gave analytically pure product, mp 203°–204° C.

$^1$H NMR (DMSO-d$_6$) δ9.47 (br t, 1H, J=6 Hz), 8.03 (s, 1H), 8.01 (s, 1H), 7.94 (d, 1H, J=2.1 Hz), 7.63 (t, 1H, J=6.9 Hz), 7.52–7.58 (m, 3H), 7.35 (dd, 1H, J=2.1, 8.7 Hz), 7.29 (t, 1H, J=7.8 Hz), 7.06 (s, 1H), 7.05 (d, 1H, J=6.6 Hz), 6.86 (dd, 1H, J=2.7, 7.5 Hz), 4.57 (q, 2H, J=6 Hz), 3.76 (s, 3H).

Anal. calcd for C$_{23}$H$_{19}$ClN$_2$O$_4$S: C, 60.72; H, 4.21; N, 6.16 Found: C, 60.60; H, 4.17; N, 6.12.

EXAMPLE 39

Preparation of N-(3-hydroxybenzyl)-3-phenylsulfonyl-5-chloroindole-2-carboxamide To a saturated solution of N-(3-methoxybenzyl) 3-phenylsulfonyl-5-chloroindole-2-carboxamide (1.37 g, 3.0 mmol) in dry methylene chloride (140 mL) under an inert atmosphere was added boron tribromide in hexane (1M, 10 mL, 10 mmol). After stirring for 12–20 hours, the reaction was neutralized by addition of aq. NaHCO$_3$. After two hours, the solution was made weakly acidic by addition of dilute HC$_1$. The precipitated product was collected by filtration and then the aqueous filtrate extracted with ethyl acetate. The organic layer was dried (Na$_2$SO$_4$), filtered, and the solvent evaporated. The residue was triturated with diethyl ether to give additional product. The solids were combined and crystallized from hot methanol/ethyl acetate to give analytically pure product, mp 73.5°–274.5° C.

$^1$H NMR (DMSO-d$_6$) δ9.43 (t, 1H, J=6 Hz), 8.01 (s, 1H), 7.98 (s, 1H), 7.97 (d, 1H, J=2.1 Hz), 7.63 (t, 1H, J=6 Hz), 7.52–7.58 (m, 3H), 7.35 (dd, 1H, J=2, 1, 9 Hz), 7.17 (t, 1H, J=7.8 Hz), 6.89 (s, 1H), 6.86 (s, 1H), 6.84 (s, 1H), 6.70 (dd, 1H, J=2.1, 8.4 Hz), 4.50 (d, 2H, J=6 Hz).

Anal. calcd for C$_{22}$H$_{17}$ClN$_2$O$_4$S: C, 59.93; H, 3.89; N, 6.36 Found: C, 59.91; H, 3.86; N, 6.51

EXAMPLE 40

Preparation of N-(3-nitrobenzyl)-3-phenylsulfonyl-5-chloroindole-2-carboxamide

Using the procedure described in Example 34, except for substituting 3-nitrobenzylamine hydrochloride for 2-aminomethylimidazole dihydrochloride and adjusting the amount of triethylamine accordingly, the title compound was obtained, mp 253°–254° C.

Anal. calcd for $C_{22}H_{16}ClN_3O_5S$: C, 56.23; H, 3.43; N, 8.94 Found: C, 55.98; H, 3.37; N, 8.85

EXAMPLE 41

Preparation of N-(3-aminobenzyl)-3-phenylsulfonyl-5-chloroindole-2-carboxamide (30)

A solution of N-(3-nitrobenzyl) 3-phenylsulfonyl-5-chloroindole-2-carboxamide (353 mg, 0.75 mmol) in tetrahydrofuran (25 mL) and methanol (10 mL) containing platinum oxide (70 mg) was hydrogenated with an atmospheric pressure of hydrogen for 3 hours. The degassed solution was filtered to remove catalyst and the solvents evaporated. The residue was triturated with diethyl ether to give the product. Crystallization from acetonitrile gave analytically pure product, mp 247°–249° C.

$^1$H NMR (DMSO-$d_6$) δ9.38 (t, 1H, J=6 Hz), 7.98 (s, 1H), 7.96 (d, 1H, J=2.1 Hz), 7.53–7.60 (m, 4H), 7.35 (dd, 1H, J=2.1, 9 Hz), 7.02 (t, 1H, J=7.5 Hz), 6.61 (s, 1H), 6.60 (d, 1H, J=6 Hz), 6.50 (dd, 1H, J=2.1, 8.1 Hz), 4.43 (d, 2H, J=6 Hz).

Anal. calcd for $C_{22}H_{18}ClN_3O_3S \cdot 0.25H_2O$: C, 59.45; H, 4.20; N, 9.46 Found: C, 59.43; H, 4.08; N, 9.54

EXAMPLE 42

Preparation of N-(2-methoxybenzyl)-3-phenylsulfonyl-5-chloroindole-2-carboxamide Using the procedure described in Example 38, except substituting 2-methoxybenzylamine for 3-methoxybenzylamine, the title compound was obtained, mp 235°–237° C.

$^1$H NMR (DMSO-$d_6$) δ9.39 (t, 1H, J=6 Hz), 7.99 (d, 1H, J=2.1 Hz), 7.95 (s, 1H), 7.93 (s, 1H), 7.63 (t, 1H, J=7.2 Hz), 7.50–7.57 (m, 3H), 7.29–7.44 (m, 3H), 7.06 (d, 1H, J=7.5 Hz), 6.97 (dt, 1H, J=0.9, 7.2 Hz), 4.55 (d, 2H, J=5.7 Hz), 3.85 (s, 3H).

Anal calcd for $C_{23}H_{19}ClN_2O_4S \cdot 0.2H_2O$: C, 60.24; H, 4.26; N, 6.11 Found: C, 60.19; H, 4.40; N, 6.11

EXAMPLE 43

Preparation of N-(2-hydroxybenzyl)-3-phenylsulfonyl-5-chloroindole-2-carboxamide Using the procedure described in Example 39, except substituting the 2-methoxy isomer (Example 42) for the 3-methoxy isomer described, the title compound was obtained, mp 243°–244.5° C.

$^1$H NMR (DMSO-$d_6$) δ7.99 (d, 1H, J=3 Hz), 7.98 (s, 1H), 7.97 (s, 1H), 7.63 (t, 1H, J=6 Hz), 7.51–7.57 (m, 3H), 7.33–7.38 (m, 2H), 7.14 (dt, 1H, J=1.2, 7.8 Hz), 6.89 (d, 1H, J=7.2 Hz), 6.81 (t, 1H, J=7.2 Hz), 4.52 (s, 2H).

Anal. calcd for $C_{22}H_{17}ClN_2O_4S \cdot 0.2H_2O$: C, 59.44; H, 3.95; N, 6.30 Found: C, 59.38; H, 3.70; N, 6.39

EXAMPLE 44

Preparation of N-(4-methoxybenzyl)-3-phenylsulfonyl-5-chloroindole-2-carboxamide Using the procedure described in Example 38, except substituting 4-methoxybenzylamine for 3-methoxybenzylamine, the title compound was obtained, mp 205°–206° C.

$^1$H NMR (DMSO-$d_6$) δ9.42 (br t, 1H, J=6 Hz), 8.01 (s, 1H), 7.98 (s, 1H), 7.95 (d, 1H, J=1.8 Hz), 7.64 (t, 1H, J=7.2 Hz), 7.52–7.58 (m, 3H), 7.33–7.40 (m, 3H), 6.95 (d, 2H, J=9 Hz), 4.51 (d, 2H, J=6 Hz), 3.76 (s, 3H).

Anal. calcd for $C_{23}H_{19}ClN_2O_4S$: C, 60.72; H, 4.21; N, 6.16 Found: C, 60.59; H, 4.14; N, 6.11

EXAMPLE 45

Preparation of N-(4-hydroxybenzyl)-3-phenylsulfonyl-5-chloroindole-2-carboxamide Using the procedure described in Example 39, except substituting the 4-methoxy isomer (Example 44) for the methoxy isomer described, the title compound was obtained, mp 249°–250° C.

$^1$H NMR (DMSO-$d_6$) δ9.35 (t, 1H, J=6 Hz), 7.95–7.99 (m, 3H), 7.62 (t, 1H, J=6.9 Hz), 7.52–7.57 (m, 3H), 7.35 (dd, 1H, J=1.8, 8.7 Hz), 7.25 (d, 2H, J=8.7 Hz), 6.76 (d, 2H, J=8.1 Hz), 4.46 (d, 2H, J=6 Hz).

Anal. Calcd for $C_{22}H_{17}ClN_2O_4S$: C, 59.93; H, 3.89; N, 6.36 Found: C, 59.37; H, 3.85; N, 6.25

EXAMPLE 46

Preparation of N-(3-acetylaminobenzyl)-3-phenylsulfonyl-5-chloroindole-2-carboxamide A solution of N-(3-aminobenzyl) 3-phenylsulfonyl-5-chloroindole-2-carboxamide (Examplle 41) (176 mg, 0.4 mmol) in dry tetrahydrofuran (7 mL) containing acetic anhydride (0.05 mL, 0.5 mmol) was stirred at room temperature for 16 hours. The reaction was diluted with water and extracted with ethyl acetate. The organic layer was dried ($Na_2SO_4$), filtered through charcoal, and the solvents evaporated. The residue was triturated with methylene chloride and the solid collected by filtration to give the product, mp 249°–250° C.

$^1$H NMR (DMSO-$d_6$) δ9.98 (br s, 1H), 9.39 (v br s, 1H), 7.96–8.00 (m, 3H), 7.51–7.62 (m, 6H), 7.30 (t, 2H, J=8 Hz), 7.14 (d, 1H, J=8 Hz), 4.53 (br s, 2H), 2.4 (s, 3H).

Anal. Calcd for $C_{24}H_{20}ClN_3O_4S$: C, 59.81; H, 4.18; N, 8.72 Found: C, 59.41; H, 4.09; N, 8.62

EXAMPLE 47

Preparation of N-(3-methylsulfonylaminobenzyl)-3-phenylsulfonyl-5-chloroindole-2-carboxamide (34)

To a solution of N-(3-aminobenzyl) 3-phenylsulfonyl-5-chloroindole-2-carboxamide (174 mg, 0.4 mmol) in dry tetrahydrofuran (7 mL) at room temperature under an inert atmosphere was added methanesulfonyl chloride (0.035 mL, 0.45 mmol) and triethylamine (0.7 mL, 0.50 mmol). Over a period of 20 hours, the reaction progress was monitored by tlc. Additional equivalents of methanesulfonyl chloride and triethylamine were added twice over this period to obtain complete reaction with the carboxamide. The reaction was diluted with water, acidified with dilute HCl, and the product extracted into chloroform. This organic layer was dried ($Na_2SO_4$), filtered, and the solvent evaporated. The residue was purified by chromatography on silica gel. Elution with 1% methanol/chloroform gave the bis-sulfonylated product as evidenced by two methyl group resonances in the NMR at δ3.47 and 2.98.

this material was dissolved in dimethoxyether (3 mL) and water (2 mL) and lithium hydroxide monohydrate (66 mg, 1.57 mmol) was added. The solution was heated at 60° C. for two hours. The cooled reaction was acidified with dilute HCl. Upon stirring for 2–3 hours, the product crystallized out and was collected by filtration and dried. Recrystallization from hot methanol/ethyl acetate gave analytically pure product, mp 252°–253° C.

$^1$H NMR (DMSO-d$_6$) δ9.48 (br t, 1H, J=5.4 Hz), 8.01 (s, 1H), 7.98 (s, 1H), 7.95 (d, 1H, J=1.8 Hz), 7.63 (t, 1H, J=7.2 Hz), 7.52–7.58 (m, 3H), 7.33–7.38 (m, 2H), 7.27 (br s, 1H), 7.23 (br d, 1H, J=7.8 Hz), 7.15 (d, 1H, J=7.8 Hz), 4.55 (d, 2H, J=5.4 Hz), 3.00 (S, 3H).

Anal. calcd for $C_{23}H_{20}ClN_3O_5S_2$: C, 53.33; H, 3.89; N, 8.11 Found: C, 53.26; H, 3.86; N, 8.12

EXAMPLE 48

Preparation of N-benzyl-3-phenylsulfonyl-5-chloroindole-2-carboxamide

A solution of the dimeric acid chloride (Example 27, Step B) (170 mg, 0.25 mmol) in dry tetrahydrofuran (2 mL) was added dropwise to a solution of benzylamine (0.28 mL, 2.5 mmol) in dry tetrahydrofuran (3 mL) cooled in an ice/acetone bath. The reaction mixture was left to stir for 12–20 hours as the temperature rose to ambient. The solvents were removed under vacuum and the residue partitioned between ethyl acetate and water. The ethyl acetate layer was washed with brine, dried ($Na_2SO_4$), and the solvent evaporated. The residue was crystallized from ethyl acetate/methanol to give analytically pure product, mp 249°–251° C.

$^1$H NMR (DMSO-d$_6$) δ9.47 (t, 1H, J=6 Hz), 8.02 (s, 1H), 8.00 (s, 1H), 7.95 (d, 1H, J=2.1 Hz), 7.33–7.57 (m, 10H), 4.59 (d, 2H, J=6 Hz).

Anal. calcd for $C_{22}H_{17}ClN_2O_3S$: C, 62.19; H, 4.03; N, 6.59 Found: C, 62.14; H, 4.13; N, 6.62

EXAMPLE 49

Preparation of N-(3-pyridylmethyl)-3-phenylsulfonyl-5-chloroindole-2-carboxamide (28)

Using the procedure in Example 48, except substituting 3-aminomethylpyridine for benzylamine, the title compound was obtained, mp 263°–264° C.

Anal cacld for $C_{21}H_{16}ClN_3O_3S$: C, 59.22; H, 3.79; N, 9.87 Found: C, 59.01; H, 3.79; N, 9.87

EXAMPLE 50

Preparation of N-(2-pyridylmethyl)-3-phenylsulfonyl-5-chloroindole-2-carboxamide Using the procedure described in Example 48, except substituting 2-aminomethylpyridine for benzylamine, the title compound was obtained, mp 250°–251° C.

Anal. calcd for $C_{22}H_{16}ClN_3O_3S$: C, 59.22; H, 3.79; N, 9.87 Found: C, 59.04; H, 3.73; N, 10.06

EXAMPLE 51

Preparation of N-[2-(pyridine-4-yl)ethyl]-3-phenylsulfonyl-5-chloroindole-2-carboxamide Using the procedure described in Example 48, except substituting 4-(2-aminoethyl)pyridine for benzylamine, the title compound was obtained, mp 258°–260° C.

Anal. calcd for $C_{22}H_{18}ClN_3O_3S$: C, 60.07; H, 4.12; N, 9.55 Found: C, 59.68; H, 3.84; N, 9.30

EXAMPLE 52

Preparation of N-(2-hydroxyethyl)-3-phenylsulfonyl-5-chloroindole-2-carboxamide

Using the procedure described in Example 48, except substituting 2-hydroxyethylamine for benzylamine, the title compound was obtained, mp 198°–200° C.

Anal. calcd for $C_{17}H_{15}ClN_2O_4S$: C, 53.90; H, 3.99; N, 7.39 Found: C, 54.09; H, 3.94; N, 7.25

EXAMPLE 53

Preparation of N-ethyl-3-phenylsulfonyl-5-chloroindole-2-carboxamide

Using the procedure described in Example 48, except substituting ethylamine for beenzylamine, the title compound was obtained, mp 259°–260° C.

Anal. calcd for $C_{17}H_{15}ClN_2O_3S$: C, 56.28; H, 4.17; N, 7.72 Found: C, 56.07; H, 4.11; N, 7.73

EXAMPLE 54

Preparation of N-[(2-chloropyridin-4-yl)methyl]-3-phenylsulfonyl-5-chloroindole-2-carboxamide Using the procedure described in Example 35, Step B, except substituting 2-chloro-4-aminomethylpyridine for 2-aminomethyl-1-methylimidazole, the title compound was obtained, mp 263°–265° C.

Anal. calcd for $C_{21}H_{15}Cl_2N_3O_3S$: C, 54.79; H, 3.28; N, 9.13 Found: C, 54.38; H, 3.18; N, 9.03

EXAMPLE 55

Preparation of N-cyclopropyl-5-chloro-3-phenylsulfonylindole-2-carboxamide (26)

Using the procedure described in Example 48, except substituting cyclopropylamine for benzyamine, the title compound wa obtained, mp 242°–243° C.

Anal. calcd for $C_{18}H_{15}ClN_2O_3S$: C, 57.68; H, 4.03; N, 7.47 Found: C, 57.40; H, 3.94; N, 7.43

EXAMPLE 56

Preparation of N-(cyclopropylmethyl)-3-phenylsulfonyl-5-chloroindole-2-carboxamide Using the procedure described in Example 48, except substituting cyclopropylmethylamine for benzylamine, the title compound was obtained, mp 232°–234° C.

Anal. calcd for $C_{19}H_{17}ClN_2O_3S$: C, 57.88; H, 4.50; N, 7.11 Found: C, 57.92; H, 4.34; N, 7.09

EXAMPLE 57

Preparation of 3-(4-chlorophenylsulfonyl)-5-chloroindole-2-carboxamide

Using the procedure described in Example 30 and 31, except substituting bis(4-chlorophenyl)disulfide for di(2-thiazolyl)disulfide, the title compound was obtained, mp 275°–277° C.

Anal. calcd for $C_{15}H_{10}Cl_2N_2O_3S$: C, 48.32; H, 2.81; N, 7.51 Found : C, 48.23; H, 2.84; N, 7.91

EXAMPLE 58

Preparation of 3-(3-chlorophenylsulfonyl)-5-chloroindole-2-carboxamide

Using the procedure described in Example 30 and 31, except substituting bis(3-chlorophenyl)disulfide for di(2-thiazolyl)disulfide, the title compound was obtained, mp 272°–273° C.

Anal. calcd for $C_{15}H_{10}Cl_2N_2O_3S$: C, 48.79; H, 2.73; N, 7.59 Found: C, 48.39; H, 2.70; N, 7.44

EXAMPLE 59

Preparation of 3-(3,5-dichlorophenylsulfonyl)-5-chloroindole-2-carboxamide

Using the procedure described in Example 30 and 31, except substituting bis(3,5-dichlorophenyl)disulfide for di(2-thiazolyl)disulfide, the title compound was obtained, mp 258°–260° C.

Anal. calcd for $C_{15}H_9Cl_3N_2O_3S$: C, 44.63; H, 2.25; N, 6.94 Found: C, 44.49; H, 2.24; N, 7.04

EXAMPLE 60

Preparation of 3-(2-chlorophenylsulfonyl)-5-chloroindole-2-carboxamide

Using the procedure described in Example 33, except substituting 2-chlorothiophenol for thiophenol, the title compound was obtained, mp 267° C.

Anal. calcd for $C_{15}H_{10}Cl_2N_2O_3S$: C, 48.79; H, 2.73; N, 7.59 Found: C, 48.69; H, 2.73; N, 7.62

EXAMPLE 61

Preparation of 3-(pyridin-2-ylsulfonyl)-5-chloroindole-2-carboxamide

Using the procedure described in Example 30 and 31, except substituting bis(pyridin-2-yl)disulfide for di(2-thiazolyl)disulfide, the title compound was obtained, mp 244°–246° C.

Anal. calcd for $C_{14}H_{10}ClN_3O_3S$: C, 50.08; H, 3.00; N, 12.51 Found: C, 50.31; H, 3.00; N, 12.55

EXAMPLE 62

Preparation of 3-(pyridin-3-ylsulfonyl)-5-chloroindole-2-carboxamide

Using the procedure described in Example 30 and 31, except substituting bis(pyridin-3-yl)disulfide for di(2-thiazolyl)disulfide, the title compound was obtained, mp 300° C. dec.

FAB mass spectrum: m/e=336 (M+1)

EXAMPLE 63

Preparation of 3-(pyridin-4-ylsulfonyl)-5-chloroindole-2-carboxamide

Using the procedure described in Example 30 and 31, except substituting bis(pyridin-4-yl)disulfide for di(2-thiazolyl)disulfide, the title compound was obtained, mp>260° C. dec.

FAB maes spectrum: m/e=336 (M+1)

EXAMPLE 64

Preparation of 3-[(1-methylimidazol-2-yl)sulfonyl]-5-chloroindole-2-carboxamide

Using the procedure described in Example 30 and 31, except substituting bis(1-methylimidazol-2-yl)disulfide for di(2-thiazolyl)disulfide, the title compound was obtained, mp 255°–256° C. dec.

Anal. calcd for $C_{13}H_{11}ClN_4O_3S$: C, 46.09; H, 3.27; N, 16.54 Found: C, 46.02; H, 3.28; N, 16.27

EXAMPLE 65

Preparation of N-(3-methoxybenzyl-3-(3-chlorophenylsulfonyl)-5-chloroindole-2-carboxamide Using the procedure described in Example 38, except substituting the dimeric acid chloride derived from 3-(3-chlorophenylsulfonyl)-5-chloroindole-2-carboxylic acid for that derived from 3-(phenylsulfonyl)-5-chloroindole-2-carboxylic acid, the title compound was obtained, mp 225°–226.5° C.

Anal. calcd for $C_{23}H_{18}Cl_2N_2O_4S$: C, 56.45; H, 3.71; N, 5.73 Found: C, 56.52; H, 3.70; N, 5.83

EXAMPLE 66

Preparation of N-(3-hydroxybenzyl)-3-(3-chlorophenylsulfonyl)-5-chloroindole-2-carboxamide Using the procedure described in Example 39, N-(3-methoxybenzyl)-3-(3-chlorophenylsulfonyl)-5-chloroindole-2-carboxamide was demethylated to obtain the title compound, mp 230°–231° C.

Anal. calcd for $C_{22}H_{16}Cl_2N_2O_4S$: C, 55.58; H, 3.39; N, 5.89 Found: C, 55.59; H, 3.36; N, 5.66

EXAMPLE 67

Preparation of N-[(1-methylimidazol-2-yl)methyl]-3-(3-chlorophenylsulfonyl)-5-chloroindole-2-carboxamide (23)

Using the procedure described in Example 35, except for substituting the dimeric acid chloride derived from 3-(3-chlorophenylsulfonyl)-5-chloroindole-2-carboxylic acid for that derived from 3-(phenylsulfonyl)-5-chloroindole-2-carboxylic acid, the title compound was obtained, mp 232°–234° C.

Anal. calcd for $C_{20}H_{16}Cl_2N_4O_3S$: C, 51.84; H, 3.48; N, 12.09 Found: C, 51.46; H, 3.38; N, 11.78

EXAMPLE 68

Preparation of 2-carboxamido-5-chloroindole-3-cyclopropylsulfonamide

Step A: 2-Carboethoxy-5-chloro-1-phenylsulfonylindole-3sulfonic acid

Concentrated sulfuric acid (2.50 ml, 90 mmol) was added dropwise over 5 min at 0° C. to a stirred solution of 2-carboethoxy-5-chloro-1-phenylsulfonylindole (7.28 g, 20.0 mmol) in acetic anhydride (10 ml) and dry dichloromethane (50 ml). The resulting tan solution was warmed to RT (room temperature) and after 3 hours was poured onto ice and the mixture was extracted with ethyl acetate. The ethyl acetate layer was washed with brine, dried ($Na_2SO_4$)

and evaporated in vacuo to a syrup. Residual acetic anhydride was removed by azeotroping with toluene (3×50 ml), and the residue was crystallized from dichloromethane. The dichloromethane was evaporated in vacuo to give the title compound as a tan powder:

$^1$H NMR (d$_6$ DMSO) δ1.33 (t, J=7.1 Hz, 3H), 4.33 (q, J=7.1 Hz, 2H), 7.44 (dd, J=8.9 and 2.2 Hz, 1H), 7.63 (t, J=7.6 Hz, 2H), 7.73 (t, J=7.4 Hz, 1H), 7.77 (d, J=2.2 Hz, 1H), 7.96 (d, J=8.9 Hz, 1H), 8.00 (d, J=7.6 Hz, 2H).

Step B: 2-Carboethoxy-5-chloro-1-phenylsulfonylindole-3-cyclopropylsulfonamide

Oxalyl chloride (0.90 ml, 10.3 mmol) was added to a stirred solution of 2-carboethoxy-5-chloro-1-phenylsulfonylindole-3-sulfonic acid (1.505 g, 3.39 mmol) in dry dichloromethane (15 ml) at 0° C. DMF (2 drops) was added and the solution was warmed to room temperature. More DMF (1 drop) was added and the reaction was heated to reflux. After 2 hours, the solution was cooled and evaporated in vacuo to give the sulfonylchloride as a tan solid. This was dissolved in dichloromethane (15 ml) and cyclopropylamine (0.94 ml, 13.56 mmol) and pyridine (0.5 ml) were added. The solution was heated to reflux and after 15 min was cooled, diluted with ethyl acetate and was washed with 1M HCl solution, sodium hydrogen carbonate solution and brine, dried (Na$_2$SO$_4$) and evaporated in vacuo to a gum. Methanol (5 ml) was added to give a colorless solid, and the mixture was stirred and heated to reflux for 5 min. The solids were filtered cold, washing with cold methanol (3×5 ml), and were dried in vacuo to give the title compound as colorless crystals: mp 189°–191° C.;

$^1$H NMR (CDCl$_3$) δ0.61 (m, 4H), 1.48 (t, J=7.1 Hz, 3H), 2.26 (m, 1H), 4.58 (q, J=7.1 Hz, 2H), 5.06 (br s, 1H), 7.42 (dd, J=9.0 and 2.0 Hz, 1H), 7.54 (t, J=7.6 Hz, 2H), 7.66 (t, J=7.5 Hz, 1H), 7.97 (d, J=9.0 Hz, 1H), 7.98 (d, J=2.0 Hz, 1H), 8.09 (d, J=7.6 Hz, 2H).

Step C: 2-Carboxamido-5-chloroindole-3-cyclopropylsulfonamide

A mixture of 2-carboethoxy-5-chloro-1-phenylsulfonylindiole-3-cyclopropylsulfonamide (0.42 g, 0.870 mmol) and 2:1:1 10% potassium hydroxide solution/methanol/THF (20 ml) was heated to reflux to give a clear tan solution. After 0.5 hour reflux the solution was cooled and was concentrated in vacuo to ½ volume. The solution was acidified with 1M HCl, and the resulting mixture was extracted with ethyl acetate, washed with brine, dried (Na$_2$SO$_4$) and evaporated in vacuo to a gum. The crude product was dissolved in 2% sodium hydroxide solution which was acidified with 1M HCl. The solid material was collected by filtration, washed with 1M HCl solution, and dried in vacuo to give 3-cyclopropylsulfonamido-5-chloroindole-2-carboxylic acid. Oxalyl chloride (0.58 ml, 6.65 mmol) and DMF (1 drop) were added to a stirred suspension of the acid in dry dichloromethane (10 ml). After 1 hour at room temperature the mixture was heated to reflux for 1 hour, cooled and evaporated in vacuo to a tan solid. The solid was suspended in acetone (10 ml) and 9:1 ammonium hydroxide/acetone solution (20 ml) was added. After 15 min the solution was evaporated in vacuo to 2 ml in volume and the residue was acidified with 1M HCl solution and the mixture was extracted with ethyl acetate. The ethyl acetate layer was washed with sodium hydrogen carbonate solution, dried (Na$_2$SO$_4$) and evaporated in vacuo. The resulting tan solid was purified by flash chromatography on silica (dry loaded, eluting with a chloroform/methanol gradient, 2–10% methanol), to give the title compound as colorless crystals (from ethyl acetate/hexanes): mp 236°–238° C.;

$^1$H NMR (d$_6$ DMSO) δ0.40 (m, 4H), 2.07 (m, 1H), 7.35 (dd, J=8.7 and 2.1 Hz, 1H), 7.56 (d, J=8.7 Hz, 1H), 8.01 (d, J=1.7 Hz, 1H), 8.10 (d, J=2.1 Hz, 1H), 8.22 (br s, 1H), 8.47 (br s, 1H).

EXAMPLE 69

Preparation of 2-carboxamido-5-chloroindole-3-phenylsulfonamide

Step A: 2-Carboethoxy-5-chloro-1-phenylsulfonylindole-3-phenylsulfonamide

In the manner outlined in Example 68, Step B, aniline (0.63 ml, 6.91 mmol) was added to 2-carboethoxy-5-chloro-1-phenylsulfonylindole-3-sulfonylchloride to give, after flash column chromatography on silica (dry loaded, eluting with an ethyl acetate/hexanes gradient, 20–30% ethyl acetate) the title compound as colorless crystals;

$^1$H NMR (CDCl$_3$) δ1.47 (t, J=7.1 Hz, 3H), 4.58 (q, J=7.1 Hz, 2H), 6.74 (br s, 1H), 7.11 (m, 5H), 7.31 (dd, J=9.0 and 2.2 Hz, 1H ), 7.51 (t, J=8.1 Hz, 2H), 7.57 (d, J=1.7 Hz, 1H), 7.65 (t, J=7.5 Hz, 1H), 7.87 (d, J=9.0 Hz, 1H), 7.99 (d, J=7.6 Hz, 2H).

Step B: 5-Chloro-3-phenylsulfonamidoindole-2-carboxylic acid

2-Carboethoxy-5-chloro-1-phenylsulfonylindole-3-phenylsulfonamide (0.39 g, 0.75 mmol) was dissolved in 2:1:1 10% sodium hydroxide solution/methanol/THF (20 ml) and after 2 hours the solution was acidified with 1M HCl, and the resulting mixture was extracted with ethyl acetate, washed with brine, dried (Na$_2$SO$_4$) and evaporated in vacuo to a glass. Dichloromethane (5 ml) was added to give a colorless solid, and the mixture was stirred and heated to reflux for 5 min. The solids were filtered cold, washing with cold dichloromethane, and were dried in vacuo to give the title compound as colorless crystals;

$^1$H NMR (d$_6$ DMSO) δ7.28 (t, J=7.1 Hz, 1H), 7.4 (d, J=7.2 Hz, 2H), 7.51 (t, J=7.1 Hz, 2H), 7.72 (dd, J=8.8 and 2.1 Hz, 1H), 7.86 (d, J=8.8 Hz, 1H), 8.43 (d, J=2.1 Hz, 1H), 10.25 (br s, 1H).

Step C: 2-Carboxamido-5-chloroindole-3-phenylsulfonamide

Oxalyl chloride (0.087 ml, 1.00 mmol) and DMF (1 drop) were added to a stirred solution of 5-chloro-3-phenylsulfonamidoindole-2-carboxylic acid (123 mg, 0.35 mmol) in dry THF (3 ml) at 0° C. After 1 hour at room temperature the solution was evaporated in vacuo to give a tan solid. The solid was dissolved in acetone (1 ml) and 9:1 ammonium hydroxide/acetone solution (2 ml) was added. After 0.5 hours the solution was evaporated in vacuo to a gum which was dissolved in ethyl acetate, washed with 1M HCl and brine, dried (Na$_2$SO$_4$) and evaporated in vacuo. The resulting tan solid was purified by flash column chromatography on silica (dry loaded, eluting with an ethyl acetate/hexanes gradient, 20–70% ethyl acetate) to give the title compound as colorless crystals (from dichloromethane); mp 225°–227° C.:

$^1$H NMR (d$_6$ DMSO) δ7.00 (m, 3H), 7.17 (t, J=7.3 Hz, 2H), 7.30 (dd, J=8.8 and 2.0 Hz, 1H), 7.48 (d, J=8.8 Hz, 1H), 7.93 (d, J=2.0 Hz, 1H), 8.21 (br s, 1H), 8.28 (br s, 1H), 10.34 (br s, 1H).

EXAMPLE 70

Preparation of 2-carboxamido-5-chloroindole-3-methyl(phenyl)sulfonamide

Step A: 2-Carboethoxy-5-chloro-1-phenylsulfonylindole-3-methyl(phenyl)sulfonamide In the manner outlined in Example 68, Step B, N-methylaniline was added to 2-carboethoxy-5-chloro-1-phenylsulfonylindole-3-sulfonylchloride to give, after flash column chromatography on silica (dry loaded, eluting with an ethyl acetate/hexanes gradient, 10–30% ethyl acetate) the title compound as colorless crystals (from dichloromethane/hexanes);

$^1$H NMR (CDCl$_3$) δ1.46 (t, J=7.1 Hz, 3H), 3.30 (s, 3H), 4.55 (q, J=7.1 Hz, 2H), 6.69 (d, J=2.0 Hz, 1H), 7.11 (d, J=7.0 Hz, 2H), 7.26 (m, 4H), 7.54 (t, J=7.6 Hz, 2H), 7.66 (t, J=7.4 Hz, 1H), 7.87 (d, J=8.8 Hz, 1H), 8.08 (d, J=7.6 Hz, 2H).

Step B: 5-Chloro-3-methyl(phenyl)sulfonamidoindole-2-carboxylic acid

In the manner outlined in Example 69, Step B, 2-carboethoxy-5-chloro-1-phenylsulfonylindole-3-methyl(phenyl)sulfonamide (0.39 g, 0.75 mmol) was hydrolysed in 2:1:1 10% sodium hydroxide solution/methanol/THF (20 ml, 14 h at RT (room temperature) followed by 5 min at reflux), to give the title compound (from ethyl acetate);

$^1$H NMR (d$_6$ DMSO) δ3.26 (s, 3H), 7.03 (d, J=2.2 Hz, 1H), 7.21 (m, 6H), 7.46 (d, J=8.8 Hz, 1H).

Step C: 2-Carboxamido-5-chloroindole-3-methyl(phenyl)sulfonamide

In the manner outlined in Example 69, Step C, starting with 5-chloro-3-methyl(phenyl)sulfonamidoindole-2-carboxylic acid, and after purification by flash column chromatography on silica (dry loaded, eluting with 2% methanol/chloroform), the title compound was obtained as colorless crystals (from ethyl acetate); mp 240°–242° C.

$^1$H NMR (d$_6$ DMSO) δ3.13 (s, 3H), 7.06 (d, J=2.1 Hz, 1H), 7.09 (m, 2H), 7.23 (dd, J=8.8 and 2.1 Hz, 1H), 7.26 (m, 3H), 7.48 (d, J=8.8 Hz, 1H), 8.01 (br s, 1H), 8.06 (br s, 1H).

EXAMPLE 71

Preparation of N-[2-(1-methylimidazol-4-yl)ethyl]-3-phenylsulfonyl-5-chloroindole-2-carboxamide (25)

Reaction of 3-phenylsulfonyl-5-chloroindole-2-carboxylic acid with 1-methylhistamine under the conditions of Example 37 provides the title compound.

EXAMPLE 72

Preparation of N-[2-(3-methylimidazol-4-yl)ethyl]-3-phenylsulfonyl-5-chloroindole-2-carboxamide Reaction of 3-phenylsulfonyl-5-chloroindole-2-carboxylic acid with 3-methylhistamine under the conditions of Example 37 gave the title compound, mp 257°–258.5° C.

EXAMPLE 73

Preparation of N-[(imidazol-4-yl)methyl]-3-phenylsulfonyl-5-chloroindole-2-carboxamide Reaction of the dimeric acid chloride (Example 27, Step B) with 4-aminomethylimidazole under the conditions of Example 34 provides the title compound.

EXAMPLE 74

Preparation of N-[3-(imidazol-1-yl)propyl]-3-phenylsulfonyl-5-chloroindole-2-carboxamide Reaction of the 3-phenylsulfonyl-5-chloroindole-2-carboxylic acid with 1-(3-aminopropyl)imidazole under the conditions of Example 37 gave the title compound, mp 216°–217.5° C.

EXAMPLE 75

Preparation of 3-phenylsulfonyl-5-methylsulfonyl-aminoindole-2-carboxamide (36)

Step A: 3-Phenylsulfonyl-5-nitroindole-2-carboxamide

Reaction of ethyl 5-nitroindole-2-carboxylate (*J. Amer. Chem. Soc.* 80, 4621 (1958)) with N-(phenylthio)succinimide under the conditions of Example 33, Step B, followed by oxidation to the sulfonyl product (Step C) provides a product which may be converted to the title compound with ammonium hydroxide at elevated temperature and pressure.

Step B: 3-Phenylsulfonyl-5-aminoindole-2-carboxamide

Reduction of 3-phenylsulfonyl-5-nitroindole-2-carboxamide with hydrogen under the conditions of Example 41 provides the title compound.

Step C: 3-Phenylsulfonyl-5-methylsulfonylaminoindole-2-carboxamide

Reaction of 3-phenylsulfonyl-5-aminoindole-2-carboxamide with methanesulfonyl chloride under the conditions of Example 47 provides the title compound.

EXAMPLE 76

Preparation of 4-[(5-chloro-3-phenylsulfonylindole-2-carboxamide)methyl]pyridin-2(1H)-one (37)

Step A: N-(2-methoxy-4-pyridylmethyl)-5-chloro-3-phenylsulfonylindole-2-carboxamide Reaction of the 'acid chloride dimer' product of Example 27, Step B, with 2-methoxy-4-pyridylmethylamine under the conditions of Example 27, Step C, provides the title compound.

Step B: 4-[(5-Chloro-3-phenylsulfonylindole-2-carboxamido)methyl]-pyridin-2(1H)-one Reaction of N-(2-methoxy-4-pyridylmethyl)-5-chloro-3-phenylsulfonylindole-2-carboxamide with boron tribromide in methylene chloride at 0° C. to room temperature, according to the procedure described in Example 39, provides the title compound.

EXAMPLE 77

Preparation of N-(2-amino-4-pyridylmethyl)-5-chloro-3-phenylsulfonylindole-2-carboxamide (38)

Step A: 2-amino-4-aminomethylpyridine

2-Aminopyridine-4-carbonitrile (L. W. Deady et al, *Aust. J. Chem.*, 35, 2025 (1982)) is reduced catalytically according to the procedure of D. E. Beattie et al for the preparation of 2-amino-3-aminomethyl pyridine (*J. Med. Chem*, 20, 718, (1977)) to give the title compound.

Step B: N-(2-Amino-4-pyridylmethyl)-5-chloro-3-phenylsulfonylindole-2-carboxamide Reaction of 2-amino-4-aminomethylpyridine with the dimeric acid chloride from Example 27, Step B, according to the procedure of Example 27, Step C, provides the title compound.

EXAMPLE 78

Preparation of N-(2-aminothiazol-4-ylmethyl)-5-chloro-3-phenylsulfonyl-indole-2-carboxamide Reaction of the dimeric acid chloride from Example 27, Step B, with 2-aminothiazol-4-ylmethylamine (*Chem. Ab.* 58, 4534 (1962)) under the conditions of Example 27, Step C, provides the title compound.

EXAMPLE 79

Preparation of N-cyano-5-chloro-3-phenylsulfonyl-indole-2-carboximidamide (35)

Step A: 5-Chloro-3-phenylsulfonylindole-2-carbonitrile

5-Chloro-3-phenylsulfonylindole-2-carboxamide reacts with methyl (carboxysulfamoyl)triethylammonium hydroxide inner salt (Burgess reagent) in tetrahydrofuran (THF) solvent as described by D. A. Claremon and B. T. Phillips (Tetrahedron Lett., 29, 2155 (1988)) to provide the title compound.

Step B: Ethyl 5-chloro-3-phenylsulfonylindole-2-carboximidate

5-Chloro-3-phenylsulfonylindole-2-carbonitrile is allowed to react with ethanol saturated with hydrogen chloride at 0°–10° C. for 7 days. Evaporation to dryness affords the title compound as a hydrochloride salt. The title compound is obtained as a free base by adding the reaction mixture to an ice cold solution of excess potassium carbonate and extracting the product with chloroform.

Step C: N-Cyano-5-chloro-3-phenylsulfonylindole-2-carboximidamide

Ethyl 5-chloro-3-phenylsulfonylindole-2-carboximidate is reacted with an equimolar amount of cyanamide in absolute methanol (according to the procedure of K. R. Huffman and F. C. Schaefer (J. Org. Chem., 28, 1812 (1963)). After 30–60 minutes the solvent is removed and the residue purified by silica gel chromatography to afford the title compound.

EXAMPLE 80

Preparation of N-cyclobutyl-5-chloro-3-phenylsulfonylindole-2-carboxamide (27)

Using the procedure of Example 48 but substituting cyclobutylamine for benzylamine, there is obtained the title compound.

EXAMPLE 81

Preparation of N-cyclopropyl-5-chloro-3-phenylsulfinylindole-2-carboxamide (39)

Using the procedure of Example 28, Step B, but substituting cyclopropylamine for 4-aminomethylpyridine, there is obtained the title compound.

EXAMPLE 82

Preparation of N-[(1-methylimidazol-2-yl)methyl]-3-phenylsulfinyl-5-chloroindole-2-carboxamide (20)

Using the procedure of Example 28, Step B, but substituting 2-aminomethyl-1-methylimidazole for 4-aminomethylpyridine, there is obtained the title compound.

EXAMPLE 83

Preparation of N-[(1-methylimidazol-4-yl)methyl-3-phenylsulfonyl-5-chloroindole-2-carboxamide (21) and N-[(1-methylimidazol-5-yl)methyl]-3-phenylsulfonyl-5-chloroindole-2-carboxamide (22)

Step A: N-[(Imidazol-4(or 5)-ylmethyl]-3-phenylsulfonyl-5-chloroindole-2-carboxamide Employing the procedure of Example 34, but substituting 4(or 5)-aminomethylimidazole dihydrochloride for 2-aminomethylimidazole dihydrochloride, there is obtained the title compound.

Step B: N-[(1-methylimidazol-4-yl)methyl]-3-phenylsulfonylindole-5-chloroindole-2-carboxamide; N-[(1-methylimidazol-5-yl)methyl]-3-phenylsulfonyl-5-chloroindole-2-carboxamide Employing the procedure of Example 36, but substituting N-[(imidazol-4(or 5)-yl)methyl]-3-phenylsulfonyl-5-chloroindole-2-carboxamide for N-[(imidazol-2-yl)methyl]-3-phenylsulfonyl-5-chloroindole-2-carboxamide, there is obtained each of the title compounds which are obtained pure by chromatography on silica gel.

EXAMPLE 84

Preparation of N-[(R)-1-phenylethyl]-5-chloro-3-phenylsulfonylindole-2-carboxamide (33)

Employing the procedure of Example 29, but substituting (R)-(+)-α-methylbenzylamine for (S)-(+)-2-phenylglycinol, there was obtained the title compound, mp 149° C. Anal. calcd for $C_{23}H_{19}ClN_2O_3S.0.15$ $C_2H_4O_2.0.15H_2O$: C, 62.32;H,4.54;N,6.16. Found: C,62.39; H,4.54;N,6.01.

$^1$H NMR (DMSO-$d_6$) δ3.06(1H,s);9.43(1H,d,J=8 Hz); 7.94–8.02(3H,m);7.46–7.67(6H,m);7.25–7.42(4H,m);5.21 (1H,q,J=7 Hz);1.53(3H,d,J=7 Hz).

EXAMPLE 85

Preparation of N-[(1-ethylimidazol-2-yl)methyl]-3-phenylsulfonyl-5-chloroindole-2-carboxamide Using the procedure described in Example 35, except substituting 2-aminomethyl-1-ethylimidazole for the 2-aminomethyl-1-methylimidazole (Step A), the title compound was obtained, mp 204°–205.5° C.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A compound of Formula A,

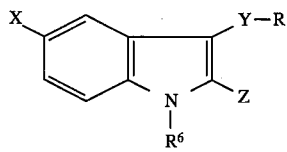

wherein

X is —H, —Cl, —F, —Br, —NO$_2$, —CN, —OR$^2$, —NR$^2$R$^2$, —NHSO$_2$—C$_{1-3}$alkyl, or —NHCO—C$_{1-3}$alkyl;

Y is —S(O)$_2$—;

R is
1) —$C_{1-5}$alkyl, unsubstituted or substituted with one or more of:
   a) —$C_{1-5}$alkyl,
   b) —$C_{1-5}$alkoxy,
   c) —OH, or
   d) aryl, unsubstituted or substituted with one or more of:
      i) —$C_{1-5}$alkyl,
      ii) —$C_{1-5}$alkoxy,
      iii) —OH,
      iv) halogen, or
      v) —$NR^2R^2$,
2) aryl, unsubstituted or substituted with one or more of:
   a) —$C_{1-5}$alkyl, unsubstituted or substituted with one or more of:
      i) —OH or
      ii) —$C_{1-5}$alkoxy,
   b) —$C_{1-5}$alkoxy,
   c) —OH,
   d) halogen, or
   e) —$NR^2R^2$,
3) —$NR^2R^3$;
Z is

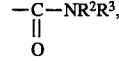

$R^2$ is hydrogen or $C_{1-3}$alkyl;
$R^3$ is
1) —$C_{1-5}$alkyl, unsubstituted or substituted with one or more of:
   a) —$C_{1-5}$alkyl,
   b) —$C_{1-5}$alkoxy, unsubstituted or substituted with —OH,
   c) —OH,
   d) —OC(O)$R^7$;
   e) —COO$R^2$;
   f) aryl, unsubstituted or substituted with one or more of:
      i) —$C_{1-5}$alkyl, unsubstituted or substituted with one or more of —OH,
      ii) —$C_{1-5}$alkoxy,
      iii) —OH,
      iv) halogen,
      v) —$NO_2$,
      vi) —$NR^2R^2$,
      vii) —NHCO—$C_{1-3}$alkyl, or
      viii) —$NHSO_2$—$C_{1-3}$alkyl,
   g) $NR^2R^2$,
   h) —$C_{3-6}$cycloalkyl,
2) aryl, unsubstituted or substituted with one or more of:
   a) —$C_{1-5}$alkyl,
   b) —$C_{1-5}$alkoxy,
   c) —OH,
   d) halogen, or
   e) —$NR^2R^2$,
3) —$C_{1-5}$alkoxy,
4) —OH,
5) —$C_{3-6}$cycloalkyl, or
6) hydrogen;
$R^6$ is hydrogen;
$R^7$ is
1) aryl, unsubstituted or substituted with one or more of —Cl, —Br, —OH, —$OCH_3$, or —CN, or —$C_{1-5}$alkyl, unsubstituted or substituted with one or more of —OH or —$NR^2R^2$;
or a pharmaceutically acceptable salt or ester thereof.

2. The compound according to claim 1 wherein:
X is —H, —Cl or —F;
R is —Ph, —tolyl, 3-Cl-phenyl,
$R^6$ is —H; and
Z is

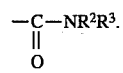

3. The compound according to claim 2 wherein:
X is —H or —Cl;
R is —Ph, —tolyl, or 3-Cl-phenyl;
$R^6$ is —H; and
Z is

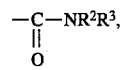

wherein $R^2$ is —H;
$R^3$ is
1) —$C_{1-5}$alkyl, unsubstituted or substituted with one or more of:
   a) —$C_{1-5}$alkoxy, unsubstituted or substituted with —OH,
   b) —OH,
   c) —OC(O)$R^7$;
   d) aryl, unsubstituted or substituted with one or more of:
      i) —$C_{1-5}$alkyl, unsubstituted or substituted with one or more of —OH,
      ii) —$C_{1-5}$alkoxy,
      iii) —OH,
      iv) halogen, or
      v) —$NR^2R^2$,
   e) —$C_{3-6}$cycloalkyl,
2) hydrogen, or
3) $C_{3-6}$cycloalkyl.

4. The compound according to claim 1 wherein X is selected from the group consisting of:
1) —$NR^2R^2$,
2) —$NHSO_2$—$C_{1-3}$alkyl and
3) —NHCO—$C_{1-3}$alkyl.

5. The compound according to claim 1 wherein Z is

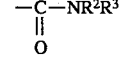

and $R^3$ is $C_{1-3}$alkyl substituted with phenyl wherein phenyl is substituted with one or more of
a) —$NO_2$,
b) —$NR^2R^2$,
c) —NHCO—$C_{1-3}$alkyl or
d) —$NHSO_2$—$C_{1-3}$alkyl.

6. A compound selected from the group consisting of:
5-chloro-3-phenylsulfinylindole-2-carboxamide, and
5-chloro-3-phenylsulfonylindole-2-carboxamide,
or a pharmaceutically acceptable salt or ester thereof.

7. A compound selected from the group consisting of
N-cyclopropyl-5-chloro-3-phenylsulfonylindole-2-carboxamide, N-cyclobutyl-5-chloro-3-phenylsulfonylindole-2-carboxamide,
N-(3-aminobenzyl)-3-phenylsulfonyl-5-chloroindole-2-carboxamide,
N-(3-methoxybenzyl)-5-chloro-3-(2-thiazolyl)-sulfonylindole-2-carboxamide,
N-[(S)-1-phenyl-2-hydroxyethyl]-5-chloro-3-phenylsulfonylindole-2-carboxamide,
N-[(R)-1-phenylethyl]-5-chloro-3-phenylsulfonylindole-2-carboxamide,
N-(3-methylsulfonylaminobenzyl)-3-phenylsulfonyl-5-chloroindole-2-carboxamide,
N-cyano-5-chloro-3-phenylsulfonylindole-2-carboximidamide,
3-phenylsulfonyl-5-methylsulfonylaminoindole-2-carboxamide, or
4-[(5-chloro-3-phenylsulfonylindole-2-carboxamido)methyl]pyridine-2(1H)-one, or
a pharmaceutically acceptable salt or ester thereof.

8. A pharmaceutical composition useful for inhibiting HIV reverse transcriptase, comprising an effective amount of a compound of any of claims 1–7, and a pharmaceutically acceptable carrier.

9. A pharmaceutical composition, comprising an effective amount of a compound of any of claims 1–7, and a pharmaceutically acceptable carrier.

* * * * *